US008112151B1

(12) United States Patent
Cogan et al.

(10) Patent No.: US 8,112,151 B1
(45) Date of Patent: Feb. 7, 2012

(54) HOUSECALL DEVICE FOR PATIENTS WITH IMPLANTED DEVICES

(75) Inventors: Donald S. Cogan, Saugus, CA (US); Ashok Kaul, Stevenson Ranch, CA (US); George L. Walls, Valencia, CA (US); Eliot L. Ostrow, Synnyvale, CA (US); Edward M. Geiselhart, Chicago, IL (US); Matthew J. Jordan, Chicago, CA (US); Bari Wieselman Schulman, Chicago, CA (US); Scott Alan Godoy, Evanston, IL (US); John S. White, Chicago, IL (US); Christopher Barry Houghton, Chicago, IL (US)

(73) Assignee: Pacesetter, Inc., Sylmar, CA (US)

( * ) Notice: Subject to any disclaimer, the term of this patent is extended or adjusted under 35 U.S.C. 154(b) by 974 days.

(21) Appl. No.: 11/766,359

(22) Filed: Jun. 21, 2007

Related U.S. Application Data

(60) Provisional application No. 60/871,389, filed on Dec. 21, 2006.

(51) Int. Cl.
*A61N 1/37* (2006.01)

(52) U.S. Cl. .......................................... 607/32
(58) Field of Classification Search .................. None
See application file for complete search history.

(56) References Cited

U.S. PATENT DOCUMENTS

| 5,544,661 | A | * | 8/1996 | Davis et al. ............... 600/513 |
| 5,720,770 | A | * | 2/1998 | Nappholz et al. ............... 607/30 |
| 2003/0144711 | A1 | * | 7/2003 | Pless et al. ..................... 607/60 |
| 2004/0116981 | A1 | * | 6/2004 | Mazar .......................... 607/60 |
| 2004/0117204 | A1 | * | 6/2004 | Mazar et al. ..................... 705/2 |
| 2006/0030890 | A1 | * | 2/2006 | Cosentino et al. ............ 607/5 |

\* cited by examiner

*Primary Examiner* — Carl H Layno
*Assistant Examiner* — Paula J Stice

(57) ABSTRACT

An exemplary device includes a processor, one or more communication interfaces, memory and one or more modules stored in the memory that comprise processor executable instructions to receive data from an implantable device via at least one of the one or more communication interfaces, to interrogate the data for one or more particular types of data, to process one or more particular types of data and to transmit information via at least one of the one or more communication interfaces. Various other exemplary devices, methods, systems, etc., are also disclosed.

16 Claims, 38 Drawing Sheets

| Number | Condition | Criteria | Level | Destination | Perm. | Msg. | QL |
|---|---|---|---|---|---|---|---|
| T1 | VT | 140 bpm | Yellow | C–X | C–X | M1 | QL1 |
| T2 | Impedance | X ohms | Red | C–X,M–Y | C–X | M4 | QL4 |
| T3 | Insurance | 60 days | Green | I–Z | I–Z | M7 | QL7 |
| T4 | Clinic | 90 days | Green | C–X,H–X | H–X | M1 | |
| T5 | Blood Pres. | T1, T7, T9 | Yellow | C–X | C–X | M3 | |
| T6 | Weight | 30 days | Green | C–X | C–X | M8 | QL8 |
| T7 | VF | 182 bpm | Red | C–X,AZ | C–X | | |
| T8 | IEGM | T1 for 10 days | Yellow | C–X | C–X | M1 | QL1 |
| T9 | A Fib | X per hour | Yellow | C–X | C–X | | |
| T10 | Dry–Wet | Change | Yellow | C–X | C–X | M2 | QL2 |
| T11 | Activity | < 10% | Red | C–X,C–Y | C–X, C–Y | M2 | QL2 |
| ... | | | | | | | |
| T(N) | | | | | | | |

505

504 — SET TRIGGER

FIG. 6

ARE YOU FEELING DIZZY?
Y    N    —1712′

CLINIC TRANSMISSION STATUS
8% COMPLETE    —1712″

DR. LEVINE REQUESTS THAT
YOU CALL THE CLINIC    —1712‴

EXEMPLARY DEVICE 2200
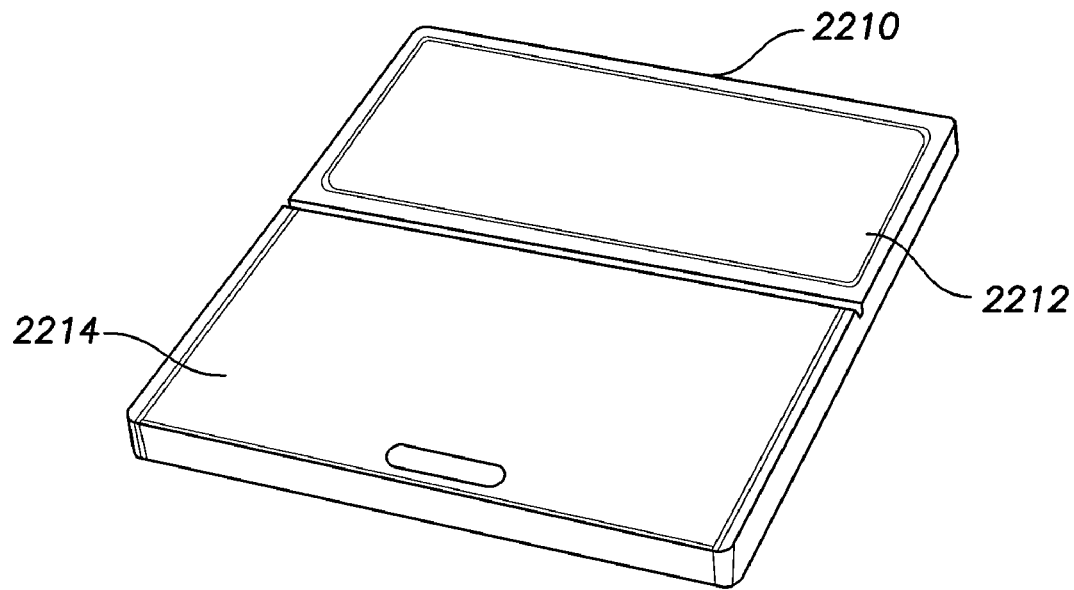
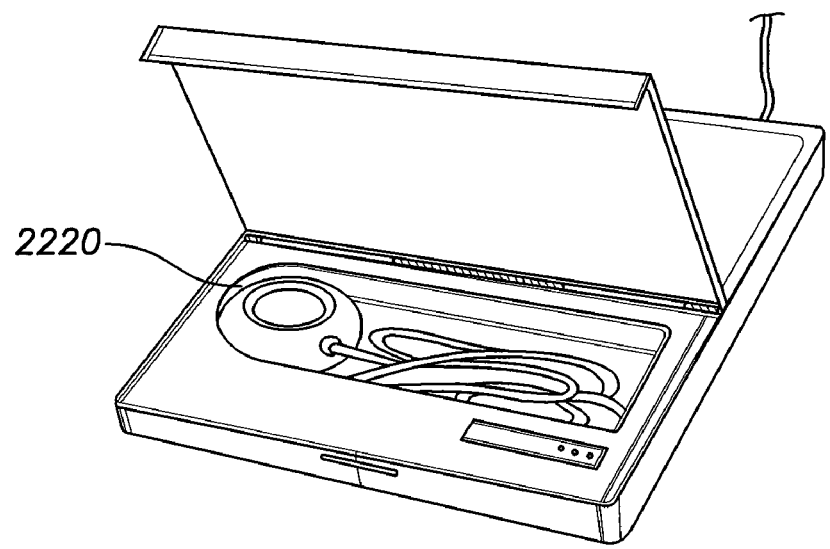
FIG. 22

FIG. 29

EXEMPLARY USER INTERFACE ~4010, 4012, 4014, 4016 — LOG OUT

| | INBOX | ARCHIVE | ADMIN. | | | |
|---|---|---|---|---|---|---|

Summary: 23 transmissions received since _____ at 4:45 pm
3 alerts and 2 transmissions viewed by provider

| Status | Patient | Device | Time | Summary | SEL | | |
|---|---|---|---|---|---|---|---|
| ⚠ | John Doe | ID-A | 3:01 pm | 2 VT-1 | ☐ | Review | Print |
| ⚠ | John Smith | ID-B | 1:34 pm | 1 VF | ☐ | Review | Print |
| | John Doe | ID-B | 1:07 pm | none | ☐ | Review | Print |
| ✓ | Julie Smith | ID-D | 11:24 am | Imp. | ☐ | Review | Print |
| ✓ | John Doe | ID-A | 10:29 am | VT-1 | ☐ | Review | Print |

[PRINT LIST]   [PRINT SEL]   [EXPORT SEL]

FIG. 30

EXEMPLARY USER INTERFACE — 4012, 4014, 4030, 4016 — LOG OUT

| Inbox | Archive | Admin. |
|---|---|---|

Jane Doe    ID-B    1:07 pm    [View Record List]   [Prev.]   [Next]

Battery [▨▨▨]    No Alerts Recorded

| Brady | VT-1 140 bpm Th1 | VT-2 140 bpm Th1a | VF 182 bpm Th3 | Episodes none |
|---|---|---|---|---|
| Summary | Tachy Episode Directory  No.   Time   Type   Therapy   Dur. | | | |

[VIEW INBOX LIST]   [PRINT]   [EXPORT]

EXEMPLARY USER INTERFACE — 4090  [LOG OUT]

┌4012 ┌4014 ┌4016
| INBOX | ARCHIVE | ADMIN. |

| | | |
|---|---|---|
| IMPORT | IMPORT RECORDS FROM MEDIA FOR REMOTE ACCESS | [IMPORT] |
| ENROLL | ENROLL A PATIENT FOR REMOTE TRANSMISSIONS | [ENROLL] |
| ACTIVATE | ACTIVATE A PATIENT WITH NEW IMPLANT | SELECT CLINIC ▼ / SELECT PATIENT ▼ [ACTIVATE] |
| ADVANCED CONFIG. | SETUP AND MANAGE ACCTS, ENROLL CLINICS AND CLINICIANS, SET PRIVILEGES | USER / PASSWORD [SUBMIT] |

FIG. 33

EXEMPLARY USER INTERFACE — 5010  [LOG OUT]

┌5012     ┌5014          ┌5016
| INBOX | PAST REPORTS | SETUP |

| STATUS | PATIENT | DEVICE | TIME | ALERT SUMMARY | REVIEW |
|---|---|---|---|---|---|
| ⚠ | JOHN DOE | ID-A | 3:01 PM | 2 VT-1 | |
| ⚠ | JOHN SMITH | ID-B | 1:34 PM | 1 VF | |
| | JANE DOE | ID-B | 1:07 PM | NONE | |
| ✓ | JULIE SMITH | ID-D | 11:24 AM | IMP. | |
| ✓ | JOHN DOE | ID-A | 10:29 AM | VT-1 | |

SELECT A PATIENT TO VIEW
SUMMARIES OF RECEIVED TRANSMISSIONS

FIG. 34

| EXEMPLARY USER INTERFACE | 5030 | | | | LOG OUT |
|---|---|---|---|---|---|
| 5012 INBOX | 5014 PAST REPORTS | | 5016 SETUP | | |

| STATUS | PATIENT | DEVICE | TIME | ALERT SUMMARY | REVIEW |
|---|---|---|---|---|---|
| ⚠ | JOHN DOE | ID-A | 3:01 PM | 2 VT-1 | |
| ⚠ | JOHN SMITH | ID-B | 1:34 PM | 1 VF | |
| | JANE DOE | ID-B | 1:07 PM | NONE | |
| ✓ | JULIE SMITH | ID-D | 11:24 AM | IMP. | |
| ✓ | JOHN DOE | ID-A | 10:29 AM | VT-1 | |

BATTERY ▮▮▮▯  NO ALERTS RECORDED

BRADY SUMMARY

| VT-1 140 BPM TH1 | VT-2 160 BPM TH1A | VF 182 BPM TH3 | EPISODES NONE |
|---|---|---|---|

LEAD ANALYSIS    ATRIUM    RV    LV
THRESHOLD
IMPEDANCE

EXEMPLARY USER INTERFACE — 5050    LOG OUT

5012 INBOX    5014 PAST REPORTS    5016 SETUP

JANE DOE  ID-B  1:07 PM    21 REMOTE TRANSMISSIONS
7 IN-CLINIC INTERROGATIONS    PREV.  NEXT

BATTERY ▮▮▮▯    NO ALERTS RECORDED

BRADY SUMMARY

| VT-1 140 BPM TH1 | VT-2 160 BPM TH1A | VF 182 BPM TH3 | EPISODES NONE |
|---|---|---|---|

TACHY EPISODE DIRECTORY
NO.    TIME    TYPE    THERAPY    DDBR

☐ MARK THIS REPORT FOR REVIEW

ANNOTATION

SAVE    PRINT    EXPORT

FIG. 36

```
EXEMPLARY USER INTERFACE  6050                          [LOG OUT]
JANE DOE
                  ┌─RECORD ARCHIVE──────────────────────────────┐
TRANSMISSION      │                                             │
  RECIEVED        │  REMOTE   07/12/XX   9:06 AM   DEVICE FUNCTIONING PROPERLY
  3:07 PM         │                                             │
                  │  REMOTE   06/07/XX   11:23 PM               │
SUMMARY           │                                             │
EPISODES          │  CLINIC   03/18/XX   1:45 PM   INCREASE LEVEL OF DRUG Y
DIAGNOSIS         │                                             │
TESTS             │  REMOTE   10/06/XX   7:10 AM   RESET PARAMETER Z
PARAMETERS        │                                             │
ADD               │                                             │
ANNOTATION        │                                             │
►VIEW ARCHIVE     │                                             │
REVIEW PREV.      │                                             │
REVIEW NEXT       │                                             │
 [CLOSE]          │  [PRINT LIST]                               │
                  └─────────────────────────────────────────────┘
```

FIG. 39

```
EXEMPLARY USER INTERFACE  6070                          [LOG OUT]
┌INBOX─6012─────────────────────────────────────┐  ┌ANNOTATION──┐
│ STATUS   PATIENT     DEVICE   TIME    ALERT SUMMARY│ JANE DOE IS│
│   ⚠     JOHN DOE     ID-A    3:01 PM    2 VT-1   │ COMPLAINING OF LACK
│   ⚠     JOHN SMITH   ID-B    1:34 PM    1 VF     │ OF ENERGY WHEN
│         JANE DOE     ID-B    1:07 PM    NONE     │ CLIMBING STAIRS AT
│   ✓     JULIE SMITH  ID-D    11:24 AM   IMP.     │ NIGHT. RATE
│   ✓     JOHN DOE     ID-A    10:29 AM   VT-1     │ RESPONSE OK
└───────────────────────────────────────────────┘  └────────────┘
 [MOVE TO APPROVED]              [VIEW ALL IN INBOX]
                                                          6014
┌APPROVED───────────────────────────────────────┐       [ARCHIVE]
│                                               │       [ADMIN.]
│                                               │        6016
└───────────────────────────────────────────────┘
 [PRINT]                         [REMOVE] [EXPORT]
```

FIG. 40

EXEMPLARY USER INTERFACE — 7010     [LOG OUT]

[TRANSMISSIONS] [PATIENTS] [CLINICIANS]

INBOX    LAST UPDATE:    05/07/XX AT 3:56 PM     INBOX 22 REVIEW COMPLETED

| SEL | PATIENT | DEVICE | TIME | SUMMARY | |
|---|---|---|---|---|---|
| ☐ | JOHN DOE | ID-A | 3:01 PM | 2 VT-1 | SELECT ACTION ▼ |
| ☐ | JOHN SMITH | ID-B | 1:34 PM | 1 VF | SELECT ACTION ▼ |
| ☐ | JANE DOE | ID-B | 1:07 PM | NONE | SELECT ACTION ▼ |
| ☐ | JULIE SMITH | ID-D | 11:24 AM | IMP. | SELECT ACTION ▼ |
| ☐ | JOHN DOE | ID-A | 10:29 AM | VT-1 | SELECT ACTION ▼ |

REVIEW COMPLETED
PRINT
EXPORT

[PRINT SEL] [EXPORT SEL] [PRINT LIST] ☐ SELECT ALL ITEMS

EXEMPLARY USER INTERFACE — 7030     [LOG OUT]

[TRANSMISSIONS] [PATIENTS] [CLINICIANS]

SEARCH    [SELECT CLINIC ▼]    [ENTER PATIENT NAME]
           UNIV. OF ZHIY
           NS HEART INST.    [SEARCH]
           CLINIC ESPANA
           METHODIST CLINIC

IMPORT    IMPORT RECORDS FROM MEDIA    [BROWSE]
           FOR REMOTE ACCESSS

ENROLL    ENROLL A PATIENT FOR    [ENROLL]
           REMOTE TRANSMISSIONS

ACTIVATE    ACTIVATE A PATIENT WITH    [SELECT CLINIC ▼]
           NEW IMPLANT    [SELECT PATIENT ▼]
           [ACTIVATE]

FIG. 42

EXEMPLARY USER INTERFACE —— 7050 [LOG OUT]

[TRANSMISSIONS] [PATIENTS] [CLINICIANS]
JANE DOE [SEL. PATIENT] [TRIGGERS] [MEDS.] [THERAPY]

| NO. | CONDITION | CRITERIA | LEVEL | DESTINATION | PERM. | QL |
|-----|-----------|----------|-------|-------------|-------|-----|
| T1 | VT | 140 BPM | YELLOW | C-X | C-X | QL1 |
| T2 | IMP. | X OHMS | RED | C-X,M-X | C-X | QL4 |
| T3 | INSTR. | 60 DAYS | GREEN | I-Z | I-Z | QL7 |
| T4 | CLINIC | 90 DAYS | GREEN | C-X,H-X | H-X | QL1 |
| T5 | BP | T1, T7, T9 | YELLOW | C-X | C-X | QL3 |
| T6 | WEIGHT | 30 DAYS | GREEN | C-X | C-X | QL8 |
| T7 | VF | 182 BPM | RED | C-X,A-Z | C-X | |
| T8 | IEGM | T1 FOR 10 DAYS | YELLOW | C-X | C-X | QL1 |

[LOGIC]

FIG. 43

EXEMPLARY USER INTERFACE —— 7070 [LOG OUT]

[TRANSMISSIONS] [PATIENTS] [CLINICIANS]
JANE DOE [SEL. PATIENT] [TRIGGERS] [MEDS.] [THERAPY]

NO. | T1 | T2 | T3 | T4 | T5 | T6 | T7 | T8 | T9 |

[LOGIC]

FIG. 44

HOUSECALL DEVICE FOR PATIENTS WITH IMPLANTED DEVICES

RELATED APPLICATIONS

This application claims priority from U.S. Provisional Application No. 60/871,389, filed Dec. 21, 2006, entitled "Housecall Device for Patients with Implanted Devices."

This application is also related to U.S. Ser. No. 11/766,370, filed Jun. 21, 2007, entitled "Housecall Device for Patients with Implanted Devices", which is fully incorporated by reference herein.

TECHNICAL FIELD

Subject matter presented herein generally relates to management of patient condition or condition of an implanted device.

BACKGROUND

A patient fitted with an implantable device should be as free as possible to behave in a "normal" manner, especially at home. However, a patient's desire for freedom should be balanced with a clinician's desire to monitor the patient and/or implanted device and to provide the highest level of care. Various technologies described herein aim to provide patients and/or clinicians with features that promote patient freedom and patient care.

SUMMARY

An exemplary device includes a processor, one or more communication interfaces, memory and one or more modules stored in the memory that comprise processor executable instructions to receive data from an implantable device via at least one of the one or more communication interfaces, to interrogate the data for one or more particular types of data, to process one or more particular types of data and to transmit information via at least one of the one or more communication interfaces. Various other exemplary devices, methods, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 6 is an exemplary trigger table that includes parameters for various triggers where the triggers may be used to gate information.

FIG. 22 is a series of perspective views of various exemplary housecall device configured as a tablet or essentially as a planar unit.

FIGS. 29-45 are diagrams of exemplary user interfaces.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Figure 1:
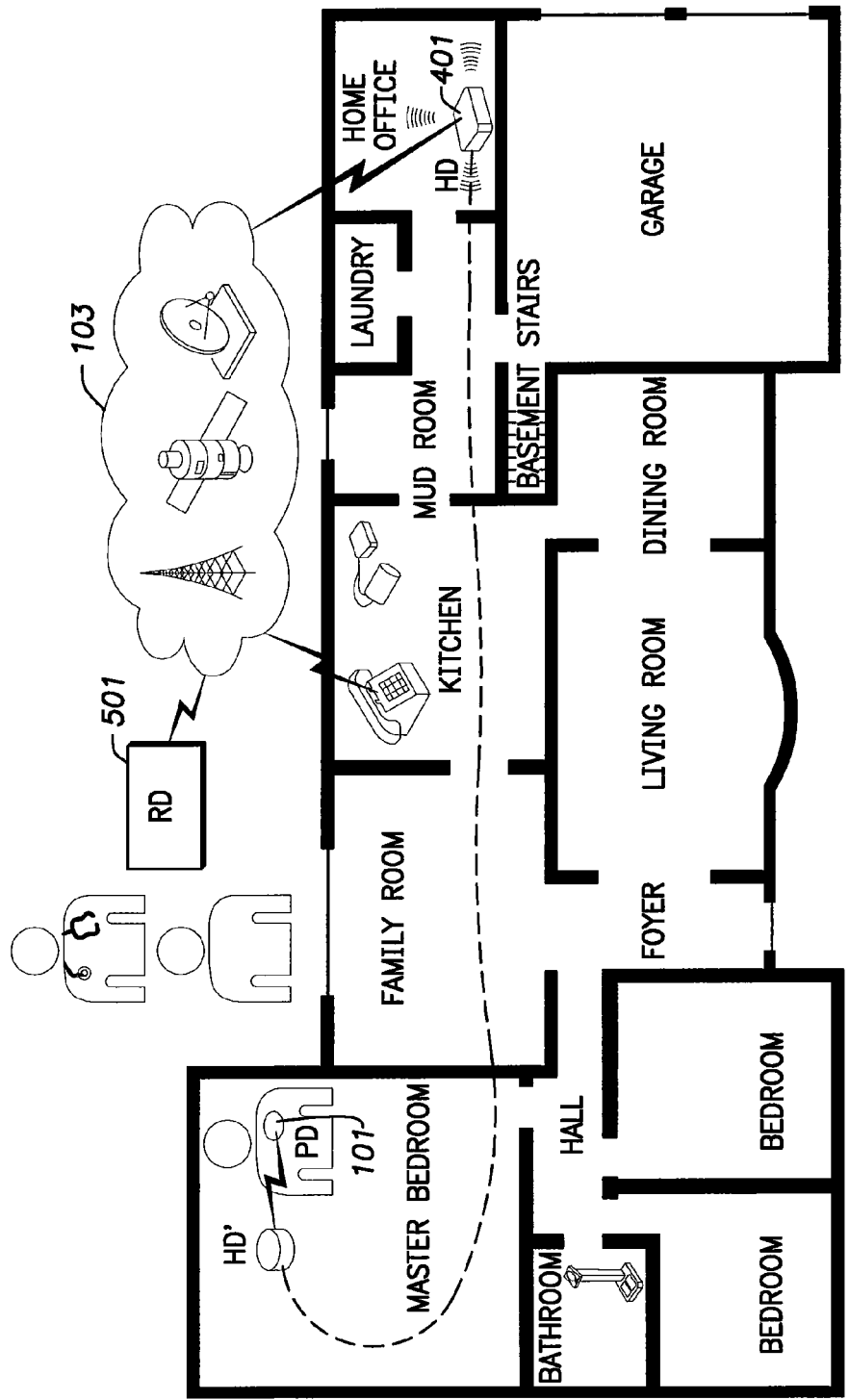
FIG. 1 is a schematic of a home environment connected to a network where a patient having an implanted device resides in the home environment and where a housecall device interacts with the implanted device and communicates via the network.

FIG. 1 shows an exemplary scenario 100 for transmission of information about a patient, an implantable patient device, another device or any combination thereof. The exemplary scenario 100 depicts a patient residing in a home where the patient has a patient device (PD) 101 that communicates with a "housecall" device (HD) 401 or a housecall satellite device (HD'). The housecall device 401 (HD) communicates via a communication network 103 with a receiving device (RD) 501. In general, the receiving device (RD) provides for notification, information or notification and information related to the patient or devices that can gather information about the patient or that can form part of a patient therapy.

FIG. 1 also shows a blood pressure meter and a scale, as examples of devices that can gather information about the patient. Such devices may be configured to communicate with the housecall device (HD) 401 or with a housecall satellite device (e.g., HD').

The communication network 103 may include more than one type of network (e.g., a heterogeneous network). The communication network 103 may rely on one or more satellites, landlines, etc. A communication link may exist between the communication network 103 and a device such as a telephone, a computer, a television, a power supply or a power meter, etc. For example, the housecall device (HD) 401, a telephone service (internet, cell or other), a television cable service, and a power service may rely on the communication network 103.

Figure 2A:
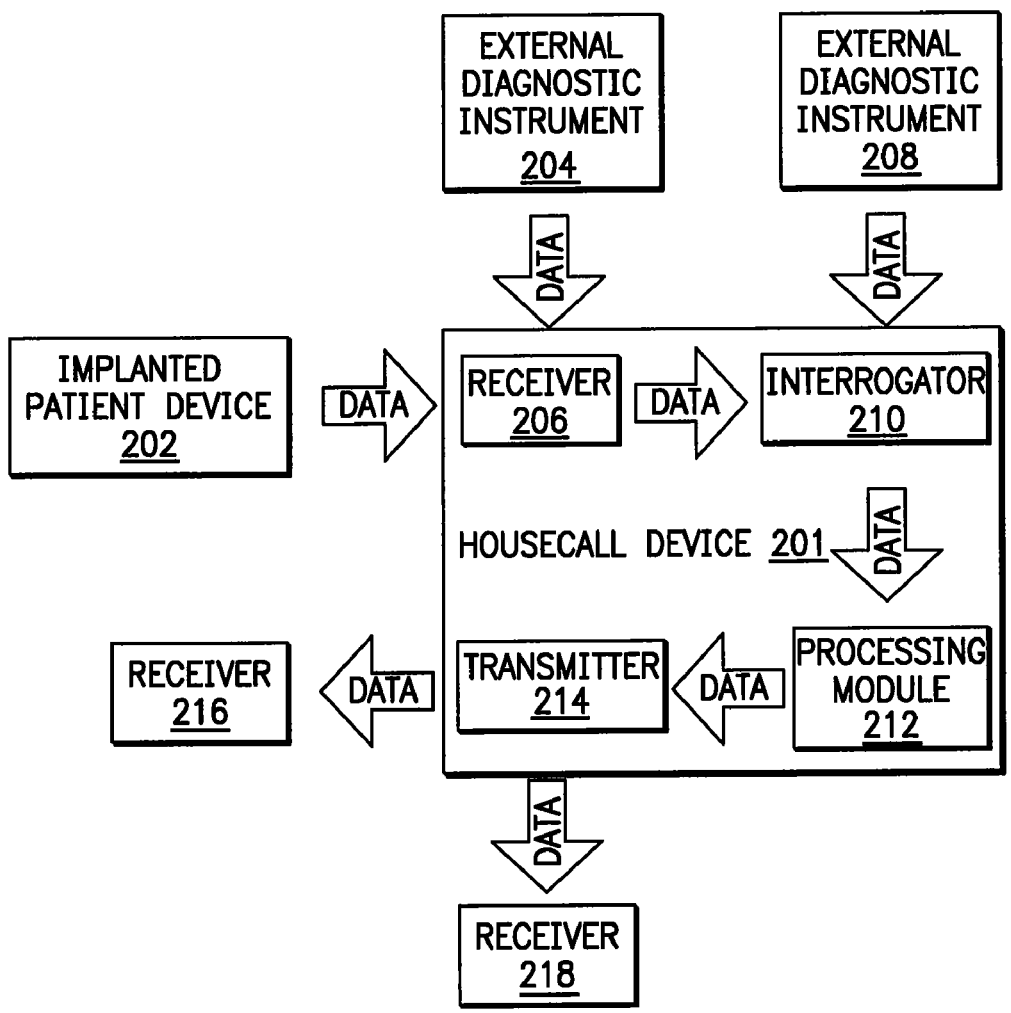
FIG. 2A is a block diagram of a scheme that includes a housecall device that receives data from an implantable device, analyzes the data and then transmits information to one or more receivers.

FIG. 2A shows an exemplary data transmission scheme 200 that includes a housecall device 201 that allows an implanted patient device 202 to transmit information from a patient environment to another environment such as a data store, a clinic, etc. In general, the patient environment is a "remote" environment as it is remote from and not associated with a conventional clinical environment or data store or data analysis environment associated with a conventional clinical environment. For example, a hospital may be a conventional clinical environment that has an on-site data store or an off-site data store for various patient records whereas a patient environment may be the home environment shown in FIG. 1, a vehicle, a backyard, etc. In general, the patient environment is defined by a patient having an implanted device, a housecall device for the patient and optionally a device or devices required for transmission of information between the patient's implanted device and the housecall device.

In the example of FIG. 2A, the housecall device 201 includes a receiver component 206 for receipt of data, an interrogator component 210, a processing module 212 for processing data and a transmitter component 214 for transmitting information. The scheme 200 includes, within a patient environment, an implanted patient device 202 and external diagnostic equipment 204 that can transmit data to the receiver component 206 of the housecall device 201.

The housecall device 201 then transmits the data from the receiver component 206 to the interrogator component 210. The interrogator component 210 acts to interrogate one or more devices (e.g., the device 202, the device 204, or the device 208). Interrogation occurs via transmission of a signal from the interrogator component 210 to a device. Upon receipt of the signal, the device then acts accordingly to transmit data to the interrogator component 210 of the housecall device.

As an alternative, or in addition to interrogation, data may be transmitted from a device to the interrogator component 210 via an operational schedule operating in the device (e.g., the device 202, the device 204 or the device 208). In yet another alternative, the interrogator component 210 may transmit a signal to a device that signals the device to take an action that may include transmitting data to a destination other than the housecall device 201.

According to the scheme 200, the interrogator component 210 transmits data to a processing module 212 for processing data. The processing module 212 typically includes logic to determine whether to transmit a notification or information. If the processing module 212 decides that such transmission or transmissions are appropriate, then a transmitter component 214 transmits the data, which may be in the form of an alert, where an "alert" is a notification. In the scheme 200, the transmitter component 214 transmits data to a receiver 216 and transmits an alert to a receiver 218.

An interrogator component may include logic to discern types of data received from an implantable device and/or other device (e.g., external diagnostic instrument, etc.). Data types may include therapy data, patient condition data and device condition data. Thus, the interrogator component may be used to parse received data, as received or on some other basis (e.g., once a day), to appropriately process data. The interrogator component may include logic that determines whether processing should occur. For example, the interrogator component 212 may use trigger or other information when making a decision to transmit data to the processing module 212.

Figure 2B:
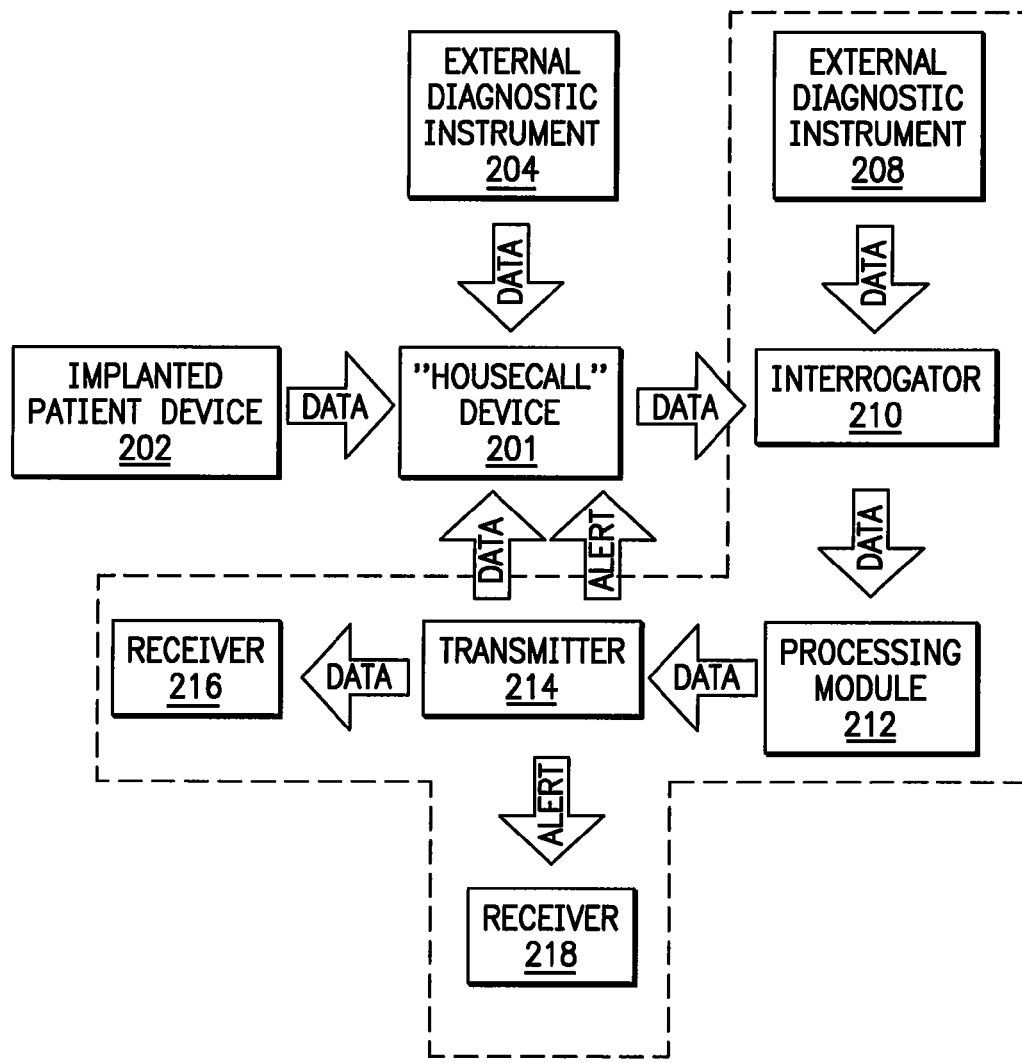
FIG. 2B is a block diagram of a scheme that includes a housecall device that receives data from an implantable device and that communicates the data to one or more other devices for analysis.

FIG. 2B shows an alternative scheme 200' where the housecall device 201 resides in a patient environment and where other components reside outside of the patient environment. In this alternative scheme 200', the housecall device 201 includes a receiver component such as the aforementioned receiver component 206.

The scheme 200' includes, within a patient environment, an implanted patient device 202 and external diagnostic equipment 204 that can transmit data to a housecall device 201. In the example of FIG. 2B, the housecall device 201 transmits the data from the patient environment to an outside interrogation environment, demarcated by a dashed line. The interrogation environment includes an interrogator 210 that acts to interrogate one or more housecall devices (e.g., the device 201). Interrogation occurs via transmission of a signal from the interrogator 210 to a housecall device 201. Upon receipt of the signal, the housecall device 201 then acts accordingly to transmit data to the interrogator 210.

As an alternative, or in addition to interrogation, data may be transmitted from the housecall device 201 to the interrogator 210 via an operational schedule operating in the housecall device 201. In yet another alternative, the interrogator 210 may transmit a signal to the housecall device 201 that signals the housecall device 201 to take an action that may include transmitting data to a destination other than the interrogator 210.

In the example of FIG. 2B, the interrogator 210 is generally a computing device configured to receive information. For example, the receiver device (RD) 501 of FIG. 1 may be an interrogator. The interrogator 210 may be control logic (e.g., software, etc.) that operates in conjunction with a computing device that performs functions in addition to interrogation.

The scheme 200' shows the interrogator 210 receiving data from the housecall device 201 as well as optionally receiving data from external diagnostic equipment 208 (arrow with dashed boundary). The external diagnostic equipment 208 may be equipment residing in a clinical environment. For example, a programmer for an implantable device may receive information from an implanted device during a patient's in-clinic visit. The interrogator 210 may then receive information from the programmer pertaining to the in-clinic visit, such as the information from the implanted device. In this manner, the interrogator 210 can receive remote information and in-clinic information.

According to the scheme 200', the interrogator 210 transmits data to a processing module 212 for processing data. The processing module 212 may operate on the same computing device as the interrogator 210. The processing module 212 typically includes logic to determine whether to transmit a notification or information. If the processing module 212 decides that such transmission or transmissions are appropriate, then a transmitter 214 transmits the data, which may be in the form of an alert, where an "alert" is a notification.

In the scheme 200', the transmitter 214 transmits data to a receiver 216, transmits an alert to receiver 218 and optionally transmits data or alerts to the housecall device 201. The scheme 200' may include open loops or closed loops. For example, a closed loop exists where data from the housecall device 201 causes the transmitter 214 to transmit data or an alert to the housecall device 201.

As described in FIGS. 2A and 2B, an exemplary scheme may include interrogation and processing (or analysis) functionality. Interrogation and analysis may occur on a relatively frequent basis or substantially continuous basis.

An exemplary scheme typically uses triggers to control flow of information. Triggers may be set based upon defined conditions (e.g., fixed or selected by a managing clinician(s)) and may be used to provide an alert to a clinician and to transmit diagnostic information. In such situations, transmitted diagnostic information is usually related to or includes information that activated the triggered to gate an alert condition to a clinician's site, remote database site, etc.

An exemplary scheme relies on triggers to control information flow via gates. For example, a trigger may cause a gate to direct information to a managing clinician only when an alert condition has taken place and when the clinician has been successfully notified that data is being transmitted for review. Where receipt of information is urgent, transmission of the information may be contingent upon a clinician acknowledging receipt of a notification.

The implanted patient device 202 of FIGS. 2A and 2B may be a pacemaker or an implantable defibrillator. The device 202 includes circuitry for transmitting specified diagnostic information (e.g. rhythm-based data, comorbidity diagnostics) utilizing a transmitter (e.g., radio frequency, microwave, etc.), which may transmit information at a designated interval or time(s) of day.

The receiver component 206 includes a receiver circuit to receive information from the device 202. The receiver component 206 may transmit a signal (e.g., a "ping") to the implanted device 202 to call for transmission of diagnostic information to the receiver component 206. The receiver component 206 may also be activated manually by a patient to prompt transmission, for example in response a patient notifier prompt from the implanted device 202.

The interrogator component 210 receives information and it may also have the capability of collecting and processing data from external instruments (e.g., instrument 204, instrument 208, etc.), directly or indirectly. Such instruments may generate information related to patient management (e.g., consider an electronic weight scale or blood pressure monitor).

The processing module 212 typically operates in concert with the interrogator component 210. The processing module 212 can assess alert conditions which may either be preset or defined by a managing clinician (e.g. blood pressure exceeding a defined limit, lead impedance out of acceptable range). As described herein, triggers are used to gate information.

Triggers are set such that upon occurrence of an event or condition, one or more gates open to allow for flow of information. Gated information may include additional data such as destination, urgency, receipt request, etc. The processing module 212 may add such additional information according to specified trigger parameters.

When a gate has been triggered, information (e.g., data, notification, etc.) is then transmitted via the transmitter module 214 to a clinic or designated service provider station, or alternatively to a web-based server for clinician access. The transmitter module 214 may send an alert message to a clinician(s) with a receiving device (e.g., the receiver 216, the receiver 218), which may be a cell phone, paging device, e-mail receiver, etc. Information transmitted to such a device may indicate the nature of the alert condition and verify successful transmission.

Figure 3:
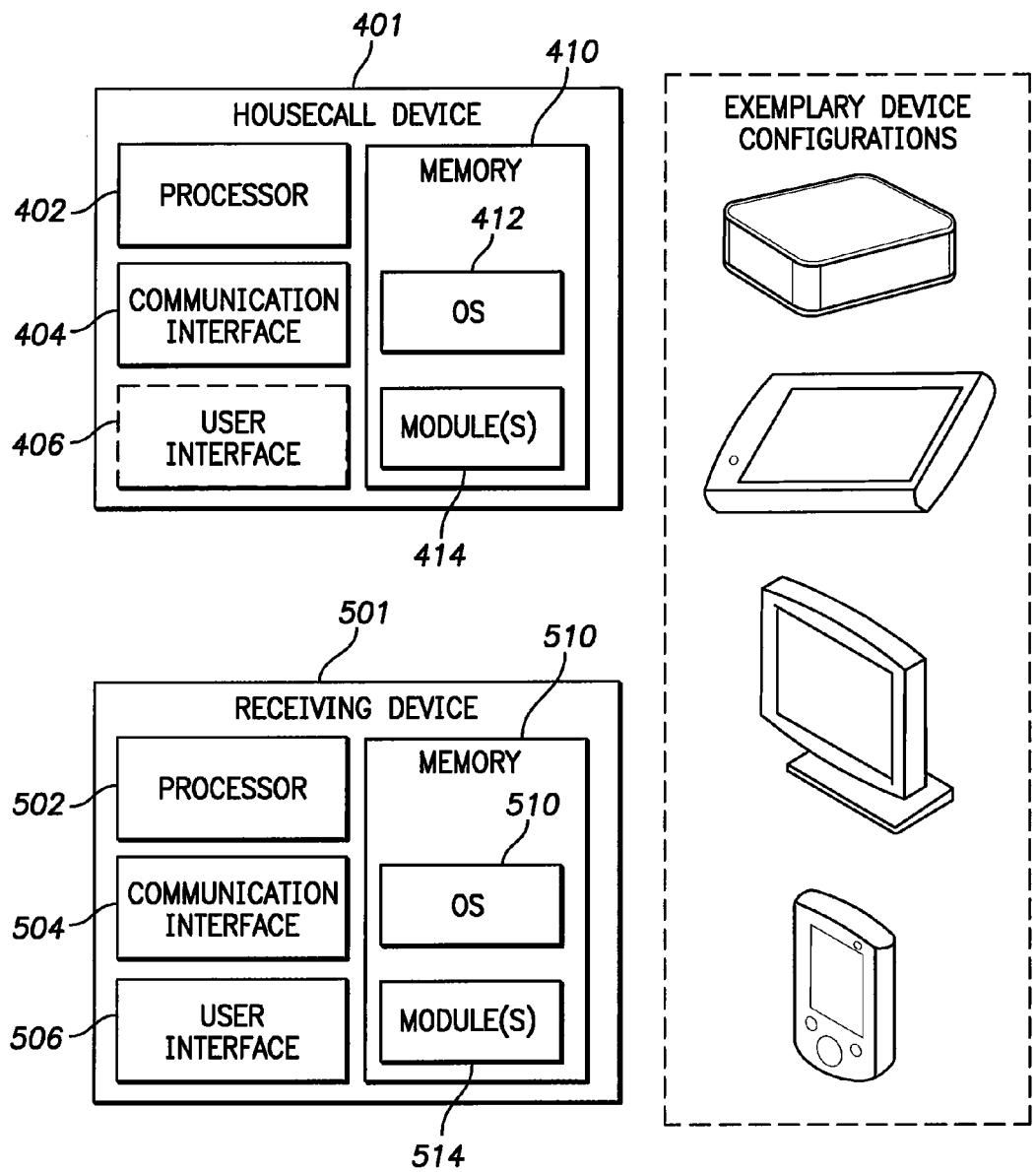
FIG. 3 is a block diagram of a housecall device and a receiving device along with various exemplary device configurations.

FIG. 3 shows various exemplary device configurations 301, a housecall device 401 and a receiving device 501. The housecall device 401 includes a processor 402, a communication interface 404 and memory 410 and optionally a user interface 406. The memory 410 stores an operating system 412 and one or more other instruction modules 414. The operating system 412 allows the processor 402 to operate according to instructions provided by an instruction module 414. In general, an instruction module 414 includes software instructions that allow the device 401 to communicate via the communication interface 404 and to optionally display or receive information via the optional user interface 406. The communication interface 404 may communicate via wire or wirelessly (consider, e.g., receiver 206 and transmitter 214). The instruction module 414 may include interrogator instructions 210 and processing instructions 212, as described with respect to FIG. 2A.

With respect to the various device configurations 301, the housecall device 401 may be a unit with or without a visual display panel. The device 401 may be battery powered, powered by house current, powered by a fuel cell, powered by a vehicle's power supply, solar powered, etc.

The receiving device 501 includes a processor 502, a communication interface 504 and memory 510 and a user interface 506. The memory 510 stores an operating system 512 and one or more other instruction modules 514. The operating system 512 allows the processor 502 to operate according to instructions provided by an instruction module 514. In general, an instruction module 514 includes software instructions that allow the device 501 to communicate via the communication interface 504 and to display or receive information via the user interface 506. The communication interface 504 may communicate via wire or wirelessly. The instruction module 514 may include interrogator instructions 210 and processing instructions 212, as described with respect to FIG. 2B.

With respect to the various device configurations 301, the receiving device 501 is typically a unit capable of displaying information via a visual display panel. The device 501 may include an integral or detachable visual display panel. The device 501 may be powered by any of a variety of power sources, however, the device 501 is typically located in a building and powered by a building's power supply.

Figure 4:
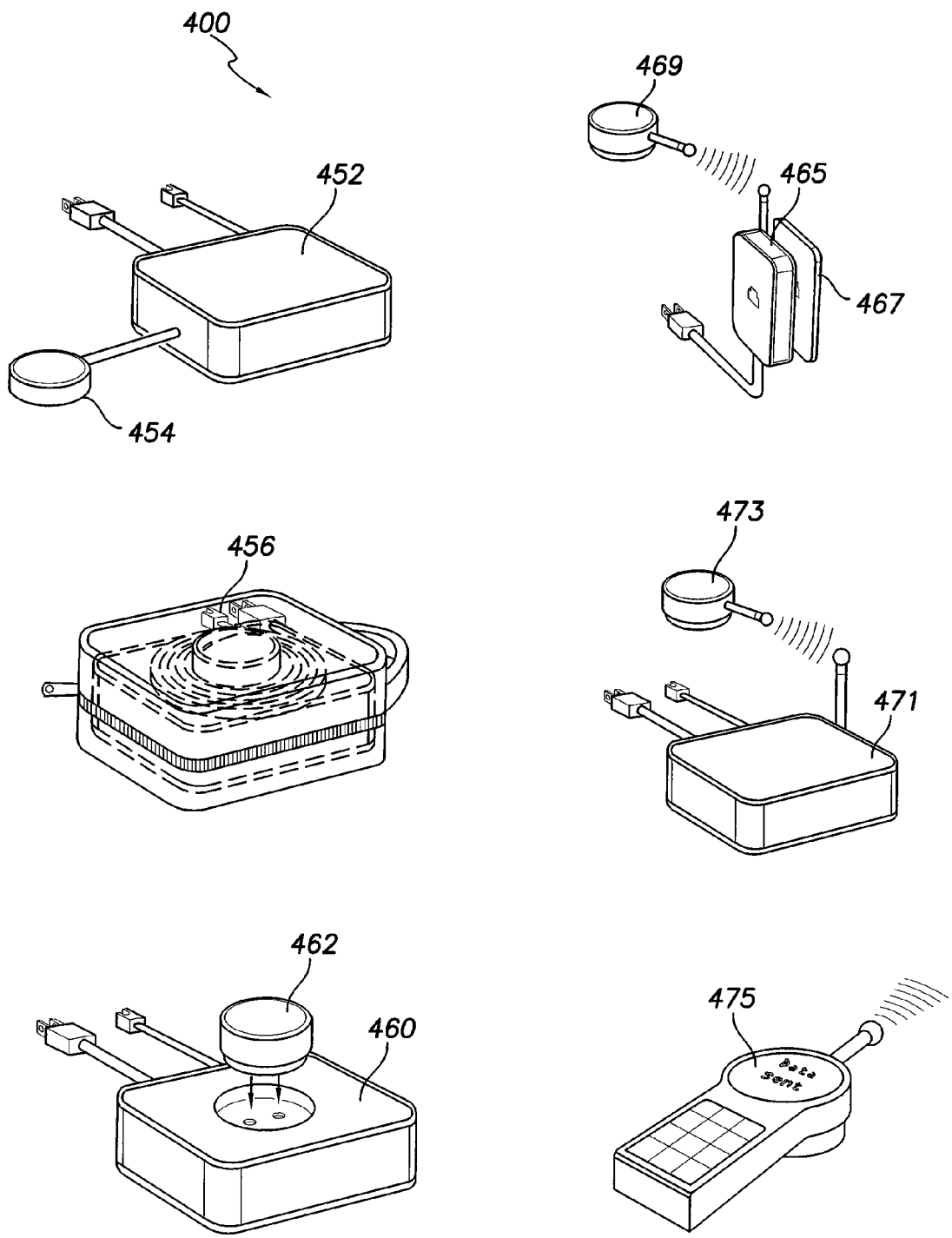
FIG. 4 is a series of perspective views of various exemplary housecall devices.

FIG. 4 shows various exemplary housecall devices 400. A device 452 includes an attached satellite unit 454 configured to receive information from an implantable device. A housecall kit 456 includes carrying case for a housecall device that optionally operates on battery power or other DC power supplies (e.g., a plane, a boat, a car, etc.). A housecall device 460 operates a base unit for a portable satellite device 462 where the base unit includes a power supply line and a communication line. In this example, the portable satellite device 462 includes a power supply that allows for operation of a communication interface to communicate with an implantable device.

A housecall assembly includes a base unit 465 that connects to a communication interface 467 such as a telephone line or a cable line. In this example, the base unit 465 includes a power cord, however, other examples may receive power via the communication interface (e.g., consider a conventional telephone, a USB bus, a Firewire bus, etc.). A satellite device 469 includes an antenna for communicating information to or from the base unit 465. In general, the satellite device 469 is configured to communicate with an implantable device.

A housecall device 471 operates as a base unit for a satellite device 473 where the base unit includes an antenna and the satellite device 473 includes antenna for communication of information. A housecall device 475 includes an antenna and a user interface for display of information. In this example, the device 475 also includes a keypad interface. The device 475 allows for communication with an implantable device and another device tied to a communication network. The device 475 may be handheld, for example, about the size of a cell phone or palm computing device.

Figure 5:
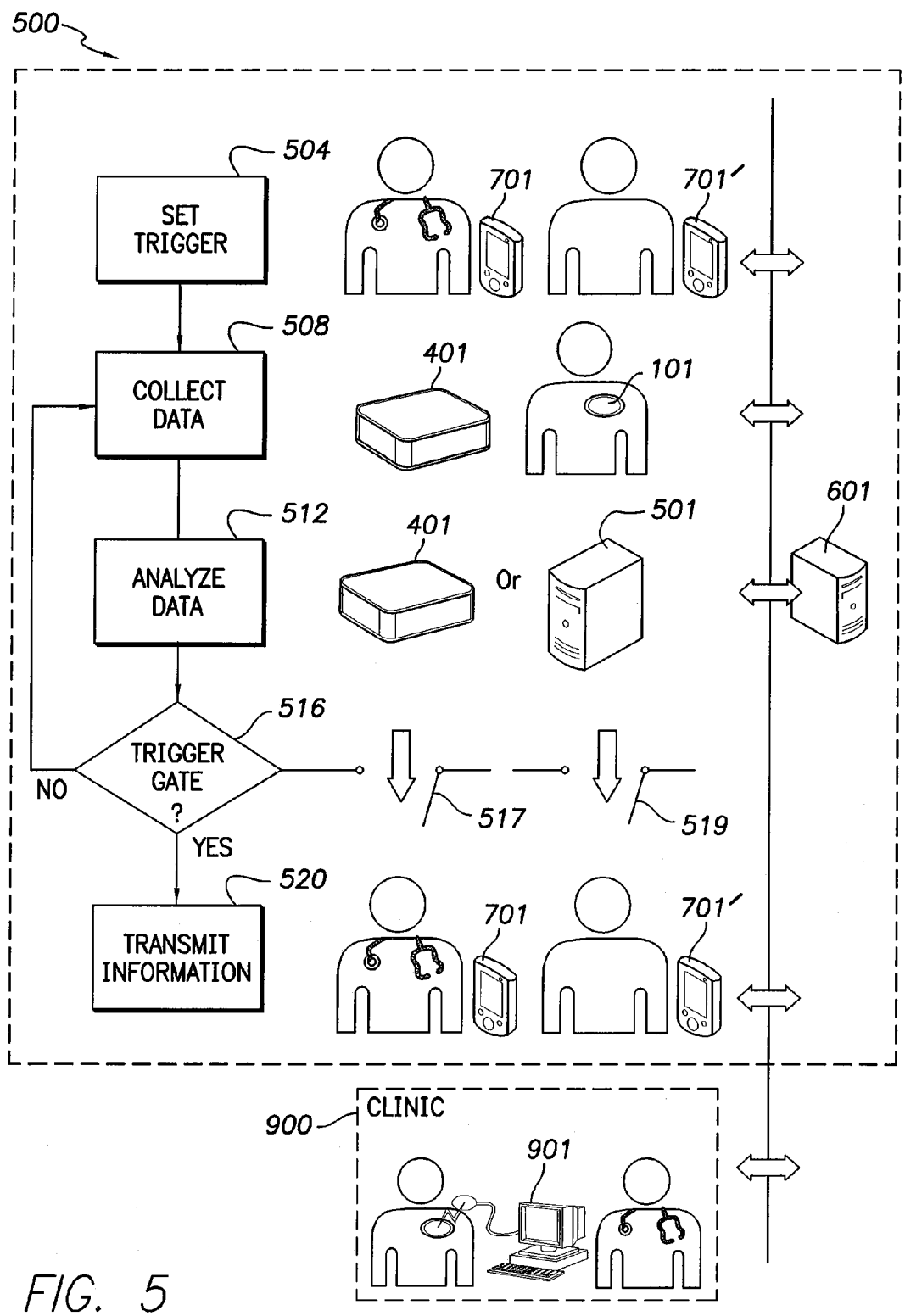
FIG. 5 is a diagram for data flow from or to a patient device and for management of such data flow.

FIG. 5 shows an exemplary remote scheme 500 for acquisition of data and communication of information responsive to a trigger along with a clinical scheme 900. In general, the scheme 500 provides for communication of information only upon occurrence of a certain condition or conditions. Such conditions cause a trigger to release or to close a communication gate. Communicated information may be simply a notice or an alert or detailed information about a patient's condition or a device's condition. While raw data from an implanted device or other device in a patient's environment may be sufficient to trigger a gate, in other instances, analysis of raw data occurs prior to triggering a gate.

The scheme 500 provides for transmitting patient-related data from a patient environment to clinical environment and can facilitate patient management. For example, the scheme 500 can reduce frequency of routine clinic visits, potentially enhancing clinician productivity by freeing up staff to manage non-routine clinic visits. The scheme 500 can also provide a significant benefit to patients who may otherwise need to travel significant distances to a clinical environment, which may be difficult or impractical. Given an ability to transmit data from a patient's environment, whether on demand by a clinician or patient initiated, can allow a clinician (or staff) to be alerted of clinical problems or device-related issues and thus be prompted to take appropriate action.

The trigger and gate scheme 500 of FIG. 5 can reduce the risk of overwhelming a clinician with an overabundance of information, for example, by identifying events or information that is particularly relevant. Further, urgency criteria or indicators may be included in triggers or gates so as to ensure that relevant information is reviewed in a timely manner.

The scheme 500 may call for collection of diagnostic data on a frequent basis, while transmitting the data with the appropriate "alert" information only when the collected data has triggered an alert condition which would warrant the immediate attention of a clinician.

The scheme 500 includes a housecall device 401 associated with a patient that has an implanted device 101. As already described, the housecall device 401 can acquire information from the implanted device 101. The housecall device 401 can then transmit the acquired information, directly or indirectly, to a receiving device 501 for analysis or the housecall device 401 may perform analysis of information. One or more gates 517, 519 control the flow of information from the housecall device 401 or the receiving device 501 (or other device, e.g., the computing device 601) to another device, a clinician or other person (e.g., insurer, spouse, etc.).

A block diagram outlines a process for transmitting information responsive to a trigger. In a set block 504, a trigger is set. For example, a clinician may use a computing device 701 to review a patient's record and to set a trigger based on the review. In another example, an insurer may note a change in the required frequency of in-clinic visits for a patient and set a trigger based on this change.

After setting a trigger 504, a data collection block 508 acts to collect data from a patient's implanted device. For example, the housecall device 401 may acquire data from the implanted device 101. Next, an analysis block 512 analyzes the acquired data. The analysis may be carried out by a housecall device 401 or another device (e.g., the device 501 or the device 601). In the example of FIG. 5, a decision block 516 decides whether to trigger a gate based on the analysis. Once triggered, a gate (e.g., the gate 517 or the gate 518) causes a transmit block 520 to transmit information. As shown in FIG. 5, the gate 517 pertains to a clinician having a computing device 701 whereas the gate 519 pertains to a non-clinician having a computing device 701'. Information may flow to the device 701 or the device 701' directly or indirectly from the housecall device 401, the receiving device 501 or the computing device 601.

FIG. 6 shows the set trigger block 504 and an exemplary table of triggers and trigger parameters 505. The table 505 includes trigger number, trigger condition, trigger criteria, trigger level, trigger destination, trigger permissions, trigger message and trigger query logic. While a trigger number is shown in table 505, any suitable trigger identifier may be used (e.g., number, letter, symbol, other). The trigger condition may relate to a patient, a device, a business, a manufacturer, etc. Trigger criteria may be generic for all patients, generic for a class of patients or patient specific. Trigger criteria may include logic that relies on one or more other triggers. For example, T5 includes the criteria T1, T7 and T9. These are three separate criteria that can, individually, cause T5 to gate blood pressure information to clinician C-X. While the level for T5 is yellow, the level may be set according to the criteria (e.g., T7 is red, thus, where T7 triggers T5, the level for T5 may be set to red as well). Trigger criteria may depend on a frequency of another trigger. For example, T8 relies on the criterion that T1 has been triggered for 10 consecutive days. Referring to T1, while the level is yellow, if it has been triggered for 10 consecutive days, the level may rise to red. Hence, a level may depend on how often a trigger occurs or, as already mentioned, upon co-occurring triggers (e.g., T5).

The trigger destination may include one or more clinician destinations (e.g., C-X, C-Y), one or more manufacturer destinations (e.g., M-Y), one or more insurance destinations (e.g., I-Z), one or more hospital/clinic destinations (e.g., H-X), one or more emergency medical service destinations (e.g., ambulance A-Z), etc. A trigger may gate information to multiple destinations, using a specific level for each destination. For example, T11 is for patient activity, while the table 505 lists the trigger level as red for destinations C-X and C-Y, in an alternative, the trigger level may be red for C-X and yellow for C-Y.

As the table 505 may include triggers related to many different parties, such parties may have access to the table 505. The permissions parameter indicates which party has access to the particular trigger, for example, to view or to make changes to the trigger. An insurer may have access to insurance related triggers only and may not be able to view other triggers whereas a patient's managing or primary clinician may be able to view, edit, add or delete any trigger.

The trigger message parameter may include a set message for display on a user interface. In an alternative, the message parameter may cause execution of software, for example, script that causes display of a message or a series of messages on a user interface. As described further below, a device may include a display for displaying a series of diagnostic questions.

Given the trigger table 505, possible functions of a housecall device (e.g., the devices 201, 401, etc.) and other devices become more clear. In particular, information received by a housecall device typically relates to the trigger criteria parameter. The housecall device or another device may analyze the information to determine whether criteria has been met and hence whether to gate information to a destination.

Various other trigger parameters may be used. For example, where a return receipt is required due to urgency, a return receipt parameter may be set. If a return receipt is not received after transmission of an alert to a destination, then control logic may cause the alert to be sent to another destination until someone acknowledges receipt. Such a scheme helps to ensure that action is taken in response to an urgent alert. This particular mechanism provides a measure of assurance to an automated system and can therefore address some liability issues. Various examples of query logic "QL" are described below (see, column QL of table 505) where the query logic causes a housecall device or other device to query a patient and receive answers to such a query. Query logic may be in the form of a questionnaire or in the form of logic that presents a query based at least in part on the answer to a prior query. Query logic may present questions in a random order, in an order determined at least in part on an answer to a prior question, and/or according to a schedule (e.g., a frequency, over a number of days, etc.). Various forms of logic are discussed herein, some with respect to exemplary housecall devices, clinician user interfaces, etc., however, these forms of logic may apply to methods, devices, systems, and user interfaces, other than those of a specific example.

FIGS. 7-12 show various workflow schemes. The workflow schemes include a patient device, a housecall device and a server or other type of receiving device (i.e., not located with a patient or a housecall device). Some workflow schemes include a workstation (clinician or third party), for example, to interact with a server where the Internet may provide for connection to server.

Data/Information from a housecall device may be processed at server or at, for example, a clinician's workstation or a third party's workstation. Thus, a workstation may have specialized software for handling such processing. Processing may be distributed to varying extents between patient device, housecall, server(s) and workstation(s).

In the exemplary workflow schemes, notification may be to a patient, a clinician and/or other (e.g., third party or manufacturer). As already discussed, triggers gate data/information and may also cause more information to be acquired. In the workflow schemes of FIGS. 7-12, triggers are represented as flags that can be set and managed.

The workflow schemes of FIGS. 7-12 include a patient having an implanted device 101, a housecall device 401, a receiving device 501 and a clinician that can access information transmitted to the receiving device 501. Symbols include flags, a "thumbs-up" OK, and checkmarks. A flag indicates notification, an OK indicates that information is routine or non-urgent and a checkmark indicates that transmission of information occurred without problems.

Figure 7:
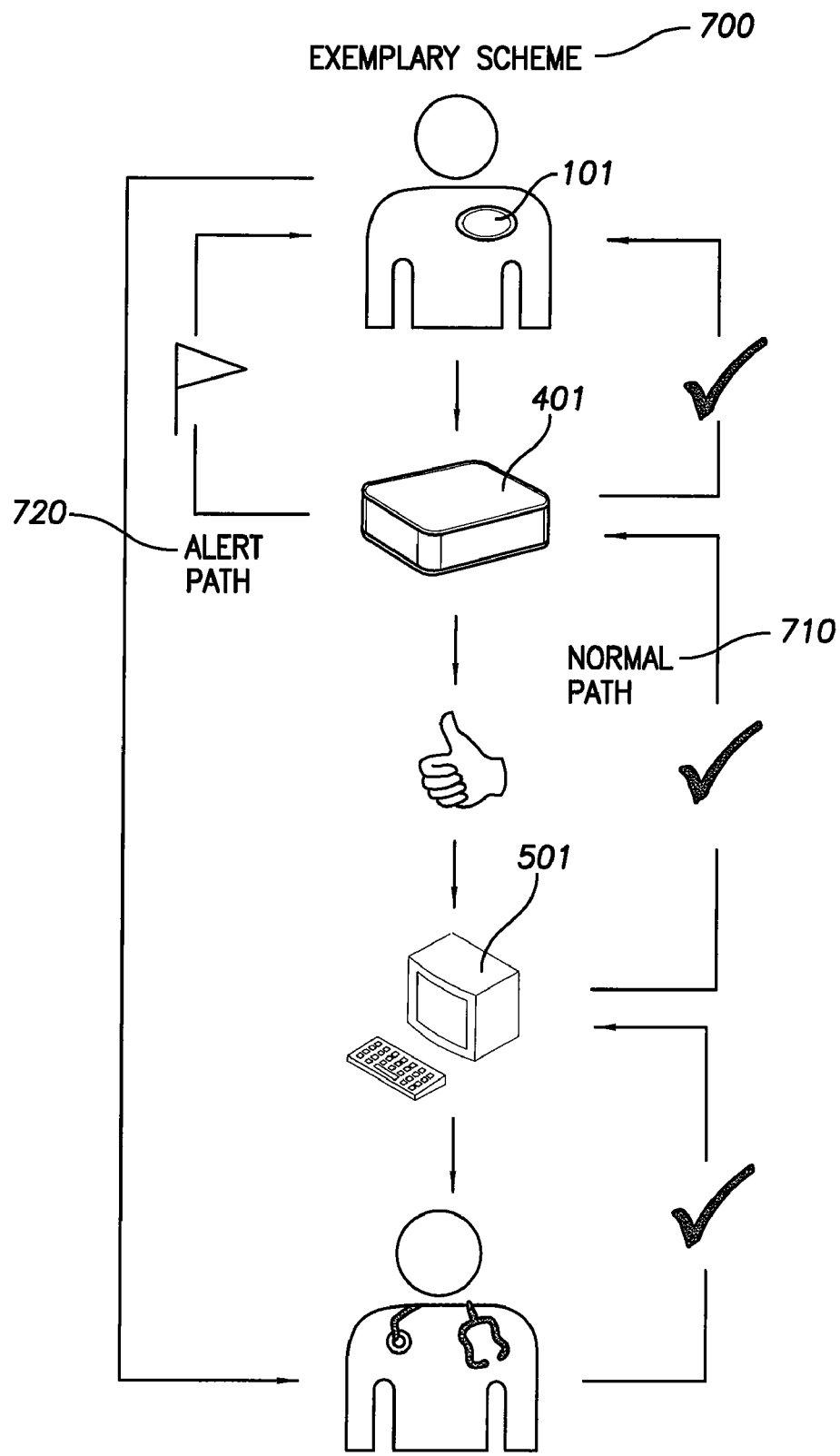
FIG. 7 is a workflow diagram of an alert path and a normal information flow path.

The workflow scheme 700 of FIG. 7 includes a patient device 101, a housecall device 401 and a server 501. The workflow scheme 700 includes a normal data flow path 710 and an alert flow path 720. The normal data flow path 710 starts with the patient device 101 sending data to the housecall device 401. In response, the housecall device 401 issues a confirmation to the patient device 101 (i.e., a checkmark). The housecall device 401 then processes the data and transmits information to the server 501. In the normal instance, where no problems exist, the information is simply routine information as indicated by the "thumbs-up" OK. In response, the server 501 issues a confirmation to the housecall device 401 (i.e., a checkmark). The clinician then reviews the information residing on the server 501 and issues a confirmation to the server 501 that the information has been reviewed (i.e., a checkmark).

The alert flow path 720 differs from the normal flow path 710 in that the housecall device 401 uncovers an anomaly in the information collected from the implanted device 101. In this instance, the housecall device 401 issues an alert to the patient. For example, the housecall device 401 may produce an audible or visual signal or transmit a signal to a device carried by the patient. In the example of FIG. 7, the patient initiates contact with the clinician to thereby notify the clinician of the alert. Where the housecall device 401 includes a display, the display may provide guidance to the patient, such as providing a telephone number for the clinician. The scheme 700 may be suitable for instances of low clinician liability where a notification goes through patient and where routine information is pushed through to the clinician.

Figure 8:
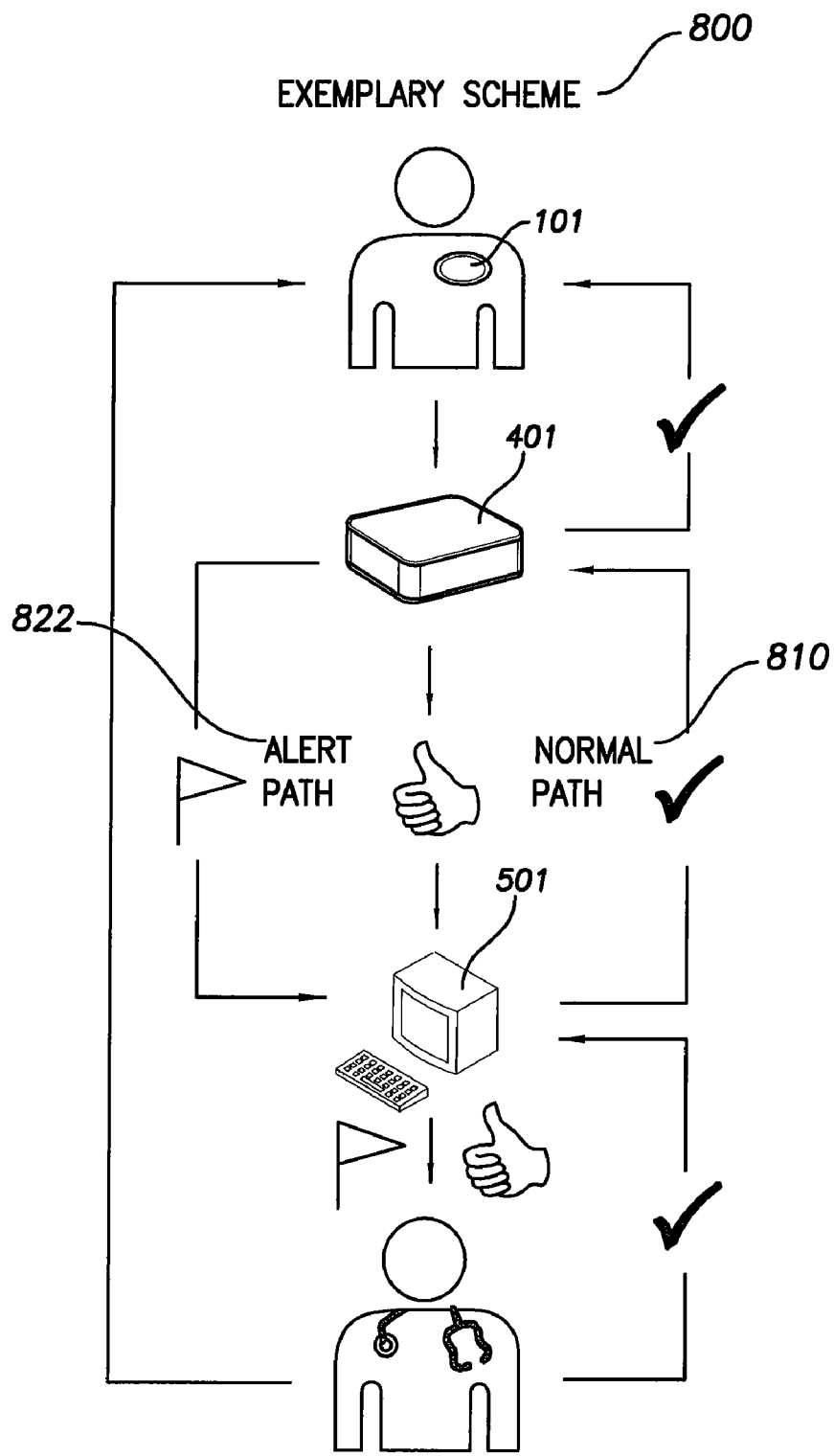
FIG. 8 is another workflow diagram of an alert path and a normal information flow path.

FIG. 8 shows an exemplary workflow scheme 800 that includes the various devices of the scheme 700. The scheme 800 includes a normal data flow path 810 and an alert flow path 822. The normal data flow path 810 operates in a manner akin to the data flow path 710. However, the alert flow path 820 differs from the alert flow path 720. In the alert flow path 822, the housecall device 401 issues an alert to the server 501 instead of to the patient. The clinician then accesses information related to the alert via the server 501 and, in turn, notifies the patient of the alert condition, as appropriate. The alert flow path 822 requires a relatively failsafe and non-disruptive notification protocol.

Figure 9:
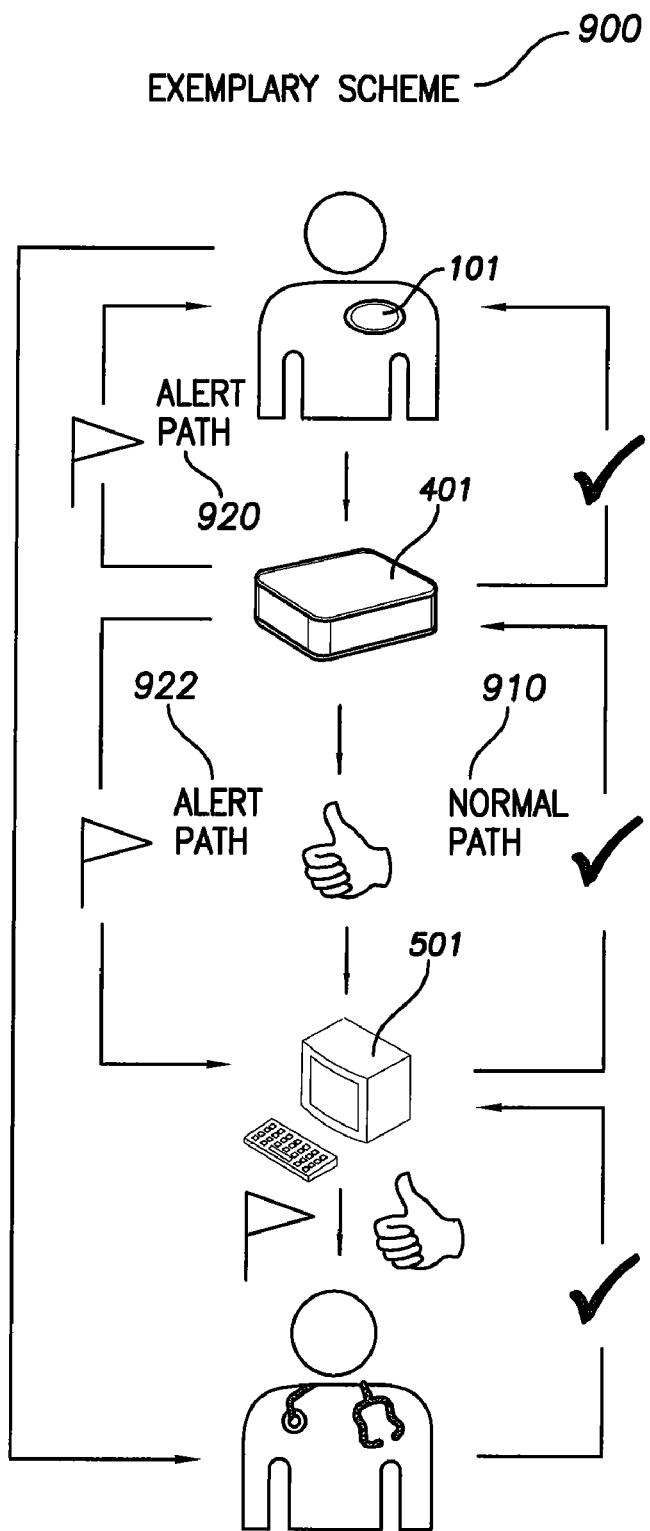
FIG. 9 is a workflow diagram of two alert paths and a normal information flow path.

FIG. 9 shows an exemplary workflow scheme 900 that includes the various devices of the scheme 700. The scheme 900 includes a normal data flow path 910 and two alert flow paths 920, 922. The normal data flow path 910 operates in a manner akin to the data flow path 710 while the alert flow path 920 operates in a manner akin to the alert flow path 720 and the alert flow path 922 operates in a manner akin to the alert flow path 822. Hence, in this example, the clinician is notified by the patient and via the server 501. Thus, the scheme 900 provides for redundant notification to the patient and the clinician while providing for transmission of routine information to the clinician.

Figure 10:
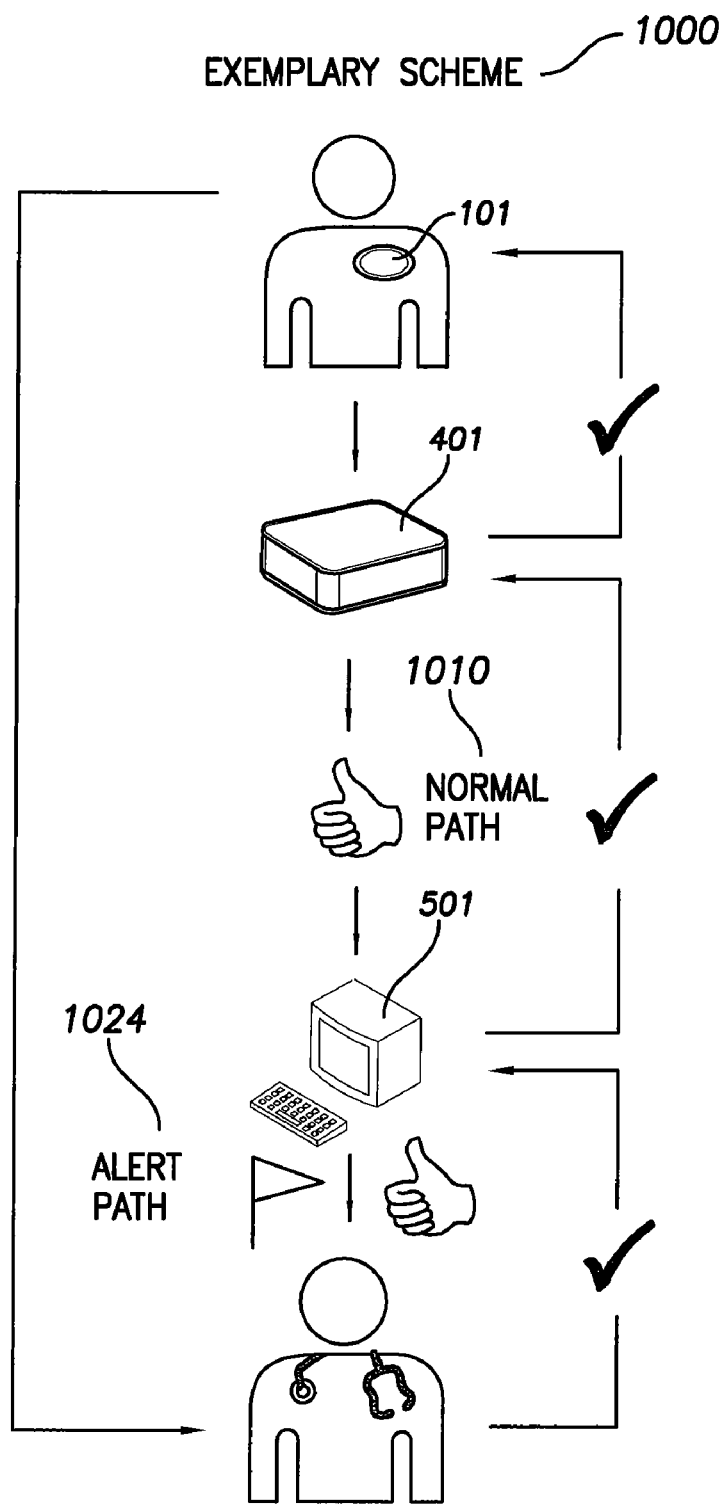
FIG. 10 is a workflow diagram of an alert path and a normal information flow path.

FIG. 10 shows an exemplary workflow scheme 1000 that includes a patient device 101, a housecall device 401 and a computing device 501. The scheme 1000 includes a normal data flow path 1010 and an alert flow paths 1024. The normal data flow path 1010 operates in a manner akin to the data flow path 710. The alert flow path 1024 differs from the alert flow paths 920 and 922. In particular, the alert flow path 1024 relies on processing information at the computing device 501, which may be a server or a workstation of a clinician. Hence, one or more processing modules for deciding whether to issue an alert exist at the computing device 501. Consequently, the alert flow path 1024 exists between the computing device 501 and the clinician. In turn, the clinician notifies the patient.

According to the scheme 1000, where data processing is provided at a server, a clinician may access the data or processed data via a network such as the Internet. Where data processing is provided at a workstation, the workstation requires processing capabilities to determine whether an alert should be issued.

Figure 11:
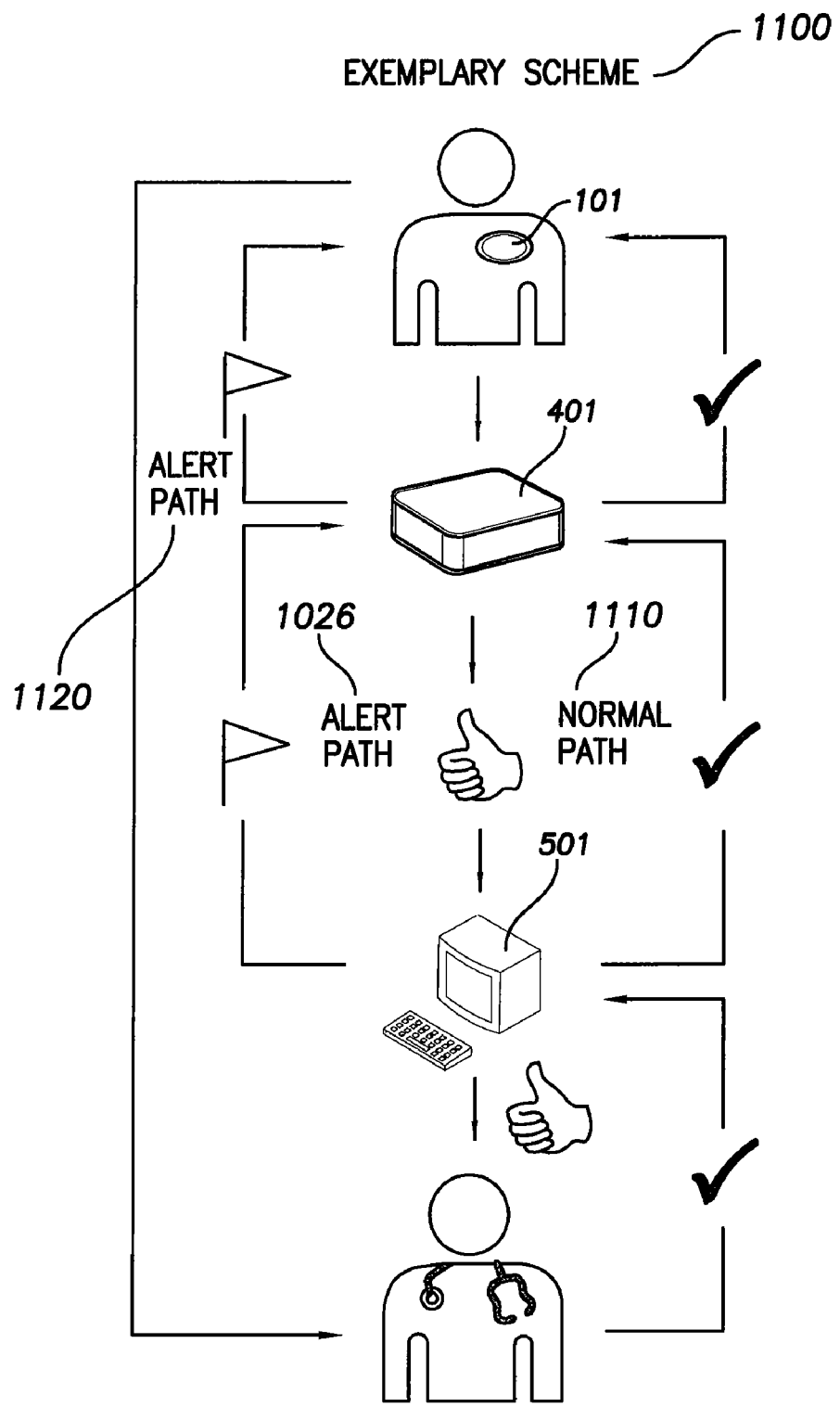
FIG. 11 is a workflow diagram of two alert paths and a normal information flow path.

FIG. 11 shows an exemplary workflow scheme 1100 that includes various devices 101, 401, and 501. The scheme 1100 includes a normal data flow path 1110 and two alert flow paths 1120, 1126. The normal data flow path 1110 operates in a manner akin to the data flow path 710 while the alert flow path 1120 operates in a manner akin to the alert flow path 720.

The alert flow path 1126 involves processing at the computing device 501 (e.g., a server or a workstation) where the processing may uncover one or more anomalies in the data. Upon uncovering such an anomaly, the device 501 issues an alert to the housecall device 401. The device 501 may be under the control of the clinician or another service provider. In general, a clinician has access to the information transmitted to the device 501. Where appropriate, a clinician may process the information and issue another alert, for example, as indicated by the alert flow path 1024 of FIG. 10. Thus, redundancies may exist for the scheme 1100.

For the scheme 1100, processing of information collected by a housecall device 401 may be performed by a third party. A clinician may have access to the information via a network (e.g., the Internet). In general, the clinician has access to routine information provided via the normal flow path 1110.

Figure 12:
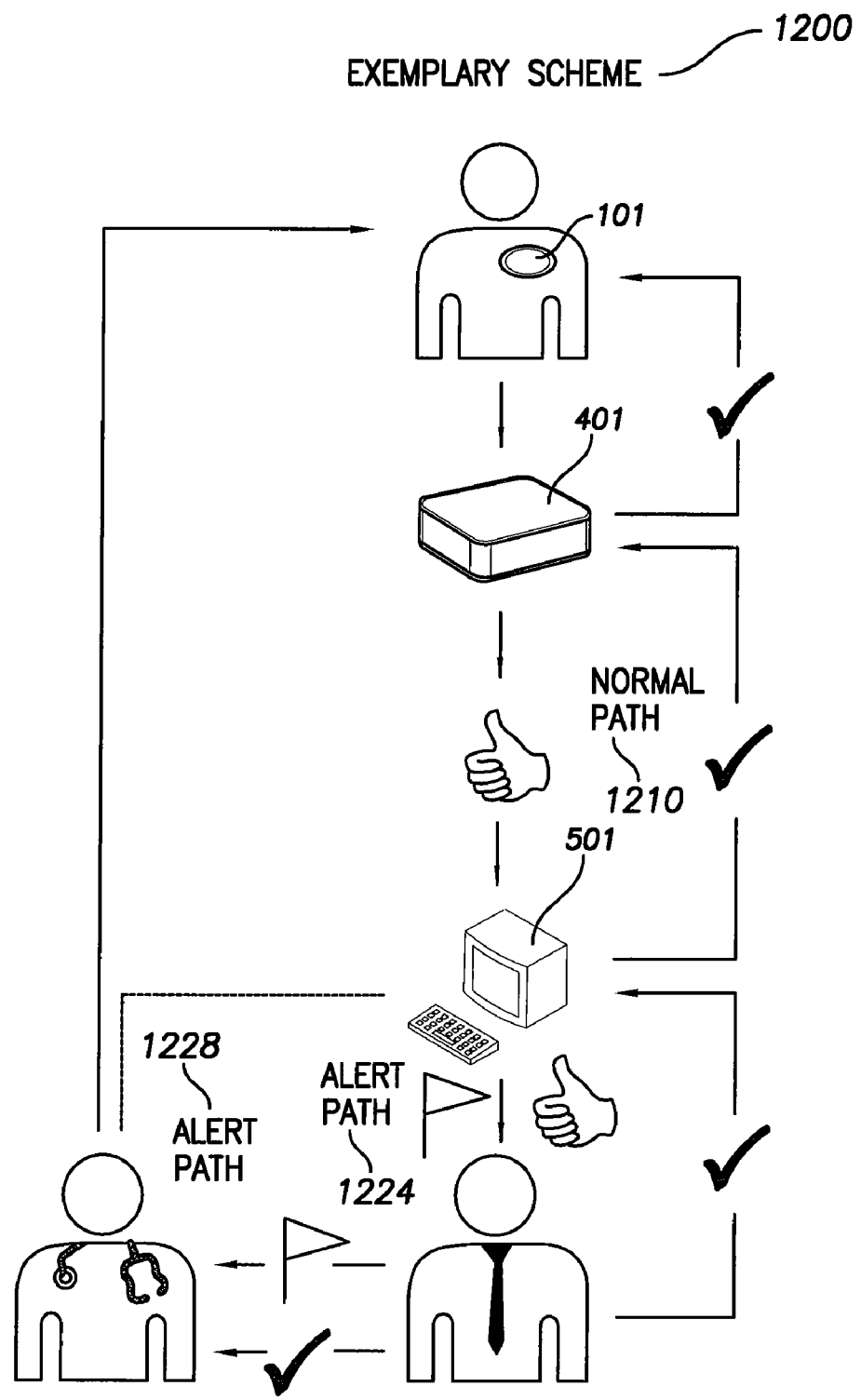
FIG. 12 is a workflow diagram of two alert paths and a normal information flow path.

FIG. 12 shows an exemplary workflow scheme 1200 that includes various devices 101, 401, and 501. The scheme 1200 includes a normal data flow path 1210 and two alert flow paths 1224, 1228. The normal data flow path 1210 operates in a manner akin to the data flow path 710, however, the information flows from the computing device 501 to a service provider other than the clinician. The computing device 501 may be a server or a workstation associated with the service provider. The alert flow path 1224 operate in a manner akin to the alert flow path 1024, however, the alert flows from the computing device 501 to a service provider other than the clinician. Consequently, the alert flow path 1228 exists between the service provider and the clinician such that the clinician can notify the patient of the alert.

In the scheme 1200, the clinician may have access to the information transmitted to the device 501 and have access to processing capabilities of the device 501 (e.g., on the same device or on a different computing device). Overall, the scheme 1200 can place responsibility on a service provider for notifying a clinician and optionally a patient of an alert. For example, another alert flow path may exist between the service provider and the patient, directly or indirectly (e.g., optionally via the housecall device 401). The service provider may provide service at a cost or in a manner that reduces demands and costs associated with the clinician. For example, the service provider may be located in one or more locations and operational 24 hours a day to thereby ensure that information is processed and alerts issued, where appropriate. Further, the service provider may act to ensure that at least one party is notified in the case of an urgent condition/alert.

Managing Flags

Figure 13:
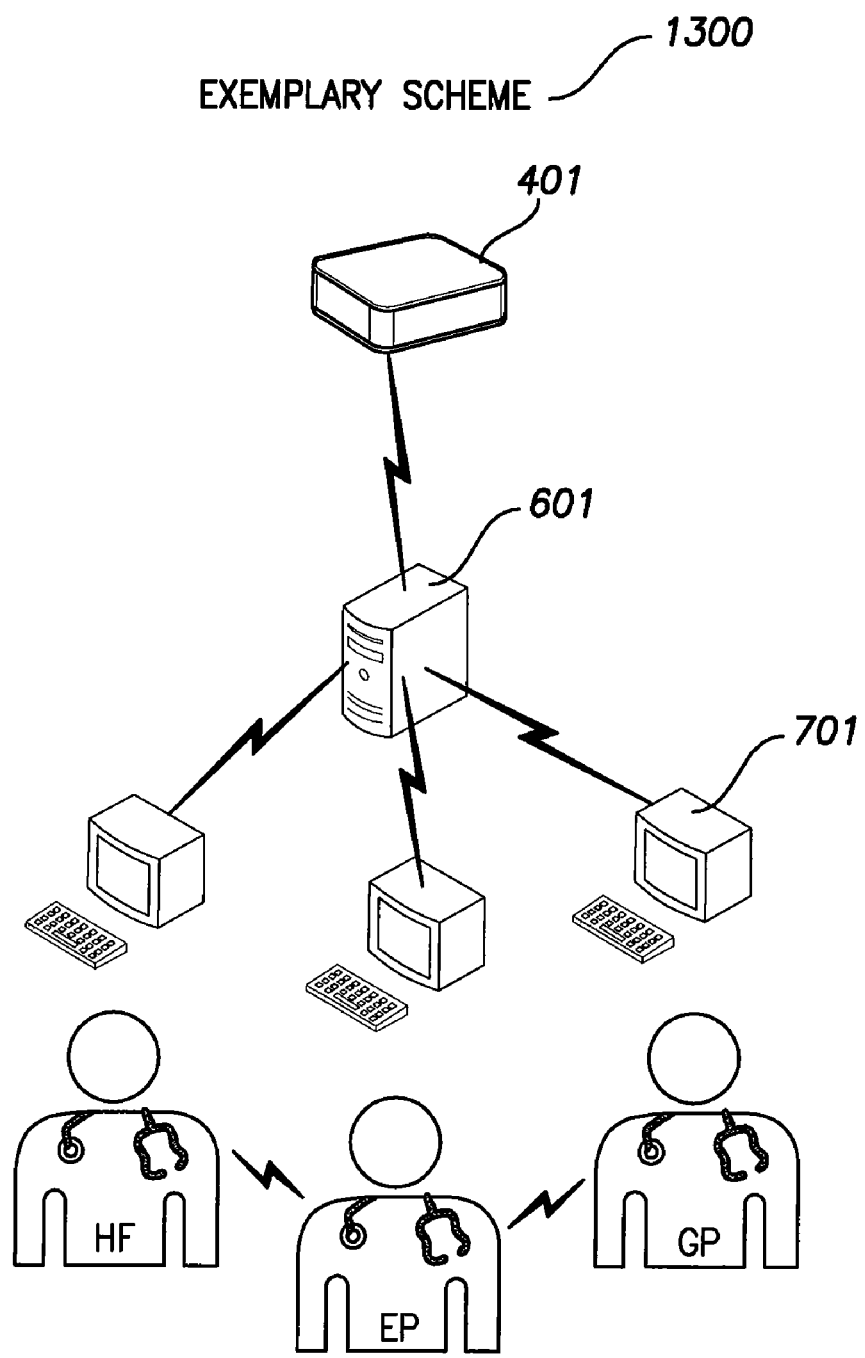
FIG. 13 is a diagram of a communication scheme for managing a housecall device.

Exemplary triggers, such as those shown in the trigger table 600, may be managed by one or more service providers. FIG. 13 shows an exemplary scheme 1300 for setting and managing triggers for a particular housecall device 401. According to the scheme 1300, a server 601 allows various service providers to access one or more triggers. In this example, the service providers include a heart failure specialist, an emergency physician and a general physician. The service providers may be in contact with each other via telephone, email or in person, for example, to discuss one or more triggers. Various terminals 701, for use by the service providers, are shown in communication with the server 601. Access to the triggers may be protected by permissions or other security measures. A trigger may be assigned a permission that limits interaction to read only, adjust only, disable only, etc.

Adjustments or changes to one or more triggers may be specific to a single patient or a single component (e.g., a housecall device) in an information chain or they may be applied to more than one patient or more than one component in an information chain and/or applied to more than one information chain.

Changes may be made globally or according to certain criteria such as version of a device's software, patient condition, etc. In some instances, a change at one site may be propagated to one or more other sites (e.g., clinicians, third parties, patients, manufacturers, patient devices, housecall devices, servers, workstations, etc.).

In the example of FIG. 13, the computing device 601 may be a server that receives information from the housecall device 401 and then processes the information. The server 601 may be accessed via a network using terminals or workstations.

Where processing and trigger management occurs at a device other than the housecall device 401, the capabilities of housecall device may be simplified. For example, a basic housecall device configuration may include a timer, memory and a communication interface to receive and transmit information.

Where processing and trigger management occurs at a service provider's workstation, the service provider may pull information from the server 601 or other data store and then process the information. For example, a service provider may receive a telephone call or an email indicating that information is at the server 601 and that the information should be reviewed or processed. In response, the service provider may log in to the server using a workstation or terminal to review or process the information and optionally manage one or more triggers.

Where processing of information occurs at the housecall device 401, the processed information and optionally the raw information may be transmitted to the server 601. In this example, triggers may operate on the housecall device 401, the server 601 or the housecall device 401 and the server 601. One or more service providers may access the server 601 via a network using a workstation or terminal 701. Such access can allow a service provider to manage triggers on the housecall device 401.

The server 601 of FIG. 13 may be associated with a particular clinic where all management of triggers occurs by a service provider at the clinic. In such a scenario, clinicians associated with the clinic interact with the service provider to manage triggers and to review information. The clinicians may interact with the service provider via email, telephone, in person, etc. In this example, the service provider may be a clinician such as a patient's primary physician.

Figure 14:
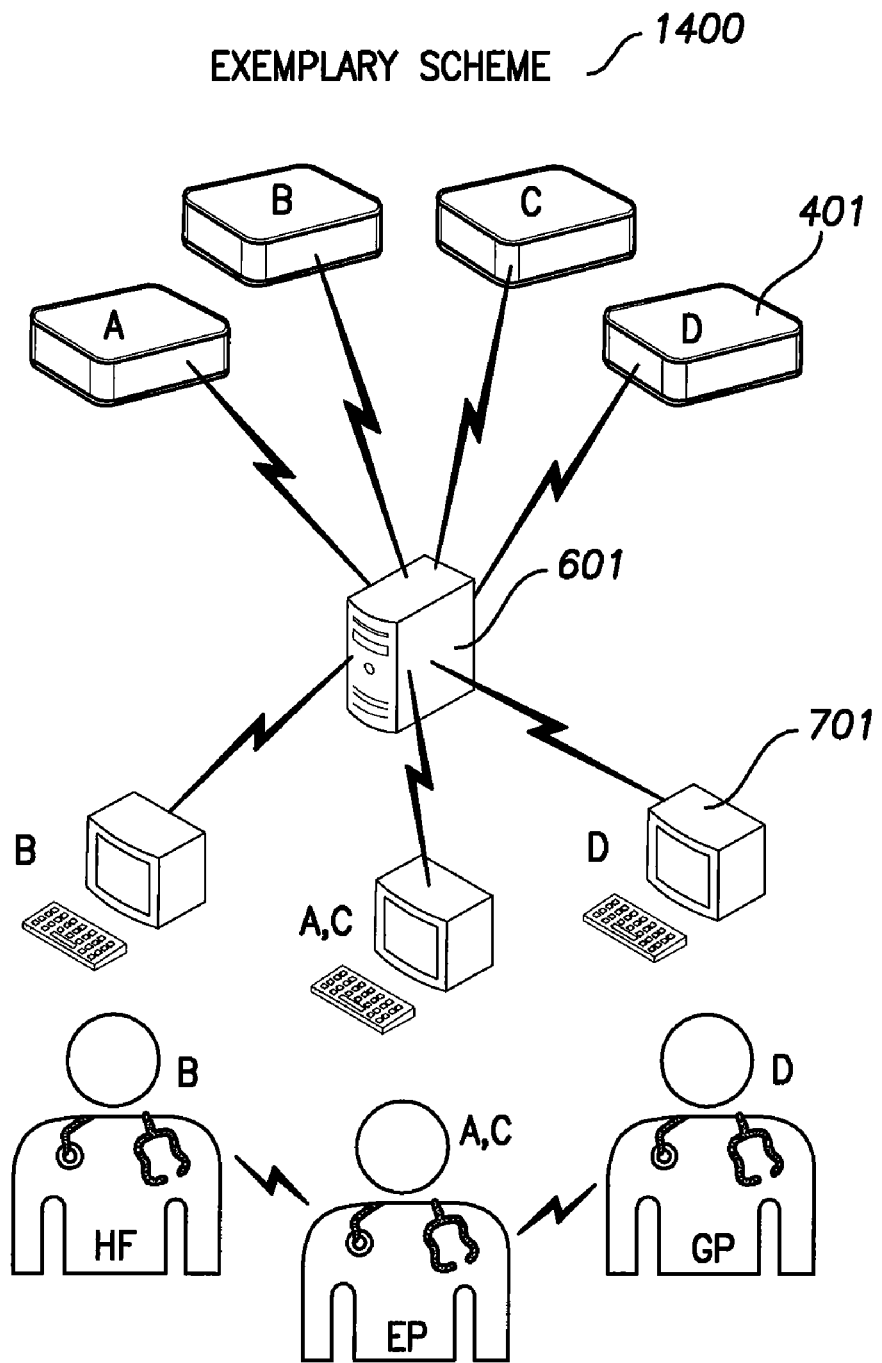
FIG. 14 is a diagram of a communication scheme for managing a plurality of housecall devices.

FIG. 14 shows an exemplary scheme 1400 that includes various housecall devices 401-A, 401-B, 401-C and 401-D, where A, B, C and D correspond to different patients where each patient has an implanted device capable of communicating, directly or indirectly, with a respective housecall device.

The computing device 601 may be a server connected to one or more communication networks. In the example of FIG. 14, a series of terminals or workstations 701 are shown in relationship to three clinicians. A heart failure clinician (HF) has responsibility for patient B, an emergency physician (EP) has responsibility for patients A and C and a general practitioner (GP) has responsibility for patient D. In other examples, a patient may have more than one assigned clinician. Permissions may restrict access to a housecall device 401, to information associated with a housecall device/patient residing on a data store, to information associated with a housecall device/patient residing on a server 601 or a workstation 701.

The scheme 1400 shows how service providers can access and manage information (e.g., diagnostic data, triggers, etc.) for an individual patient within a group of patients. Triggers may be managed to operate at the housecall device level, at the server level or at some other level (e.g., workstation, etc.). Processing of information collected from a housecall device 401 may occur at the housecall device level, the server level or at the workstation level.

Response Models

With respect to action or response schemes, various devices have been shown in communication with one or more devices or one or more communication networks. A response scheme may involve a clinician communicating with a housecall device, a clinician communicating with a patient, a housecall device communicating with a transmitter, a server communicating with a transmitter, etc.

As already mentioned, a trigger can gate information or an alert. Action or response may occur after receipt of an alert (from a patient or a device), review of alert information, or after review of routine information. A simple response to an alert may involve scheduling a visit for a patient. For example, upon receipt of such an alert by a clinic's computing device, the computing device may search a clinician's schedule and make an appointment for the patient. In instances where an alert corresponds to a class of patients or devices, the receipt of one alert may cause a clinic's computing device to search for all patients in that class or fitted with that device and then make appropriate appointments for the patients.

An exemplary scheme includes processing data with respect to triggers on a housecall device and issuing one or more notifications or alerts from the housecall device based on the processing. The notifications or alerts may be in the form of flags that can be routed via a network to a server. A clinician may log in regularly to the server and download all flags. Alternatively, a clinic may log in regularly to the server and route flags to appropriate clinicians or other service providers.

Upon receipt of a flag, a clinician may contact a housecall device directly via email or telephone. A clinician may alternatively, or in addition to, contact a patient using email, voice, voice messaging, text messaging, etc. In either instance, the clinician may communicate information germane to the condition that gave rise to the flag.

In a particular example, a clinician has a cell phone that supports text messaging and the housecall device includes a built in cell phone receiver, with a cell phone number, that supports text messaging. In this example, the clinician creates a text message and sends the text message to the phone number assigned to the housecall device.

In another example, the clinician uses a workstation to log in to a website that corresponds to the patient and the patient's housecall device. For example, the website may have a URL such a standard URL or an address that includes at least part of a patient's name or other patient identifier. The website may present a webpage (e.g., user interface) with log in fields. The housecall device may include a display panel that displays a webpage of the website. The clinician's interaction with the website may cause the housecall device to change the displayed webpage in a manner that alerts the patient. The clinician may cause the webpage to blink, display a text message, etc. Via the website, the clinician may cause the housecall device to issue an audible signal, a vibratory signal or another signal to alert the patient. An exemplary housecall device may have call forwarding service or share a cell phone number with a portable cell phone or pager carried by the patient. Communication with an exemplary housecall device may occur by any of a variety of mechanisms (e.g., 3G, GSM, WiFi, etc.).

An exemplary housecall device includes a communication interface that may select a transmission mode based on data rate. Once selected, the housecall device may transmit information according to the data rate of the selected transmission mode. For example, where the transmission mode relies on modem data rates, the information may be compressed or filtered to reduce the size of the information. Where a broadband cable line is available, the housecall device may transmit detailed information of a much larger size. Selection of transmission mode may depend on availability, size of information, urgency, etc. A trigger table may include a parameter that pertains to transmission mode.

An exemplary trigger includes a trigger parameter that causes an alert to be sent to a cell phone. The alert may include a simple text message that does not significantly delay transmission of the alert and that provides the cell phone holder with an indication of the nature of the alert.

A server may respond to a trigger by transmitting an alert to a cell phone. Also a server may include features for selection of transmission mode, where appropriate or desirable.

A housecall device optionally stores information pertaining to a patient's schedule. In particular, a housecall device may store a patient's clinical schedule. A workstation or a server may communicate with such a housecall device, directly or indirectly, to thereby read the patient's schedule and optionally alter the patient's schedule or add new schedule events (e.g., clinic visits, etc.).

Equipment Models

FIGS. 13 and 14 show various clinicians that may be part of a clinical team assigned to a particular patient or group of patients. Consequently, a communication network may exist to facilitate coordinated action of the clinical team for a patient or a group of patients.

Flow of information to the team may depend on the type of information and responsibilities of each team member. An exemplary scheme for a clinical team may include a member hierarchy to govern information flow as well as availability information for each member.

A particular scheme provides for flow of information for a heart failure specialist (HF), an emergency physician (EP) and a general practitioner (GP). The EP may use a handheld device to access a server via a network to exchange data with a housecall device. In this example, the EP may pull information from the housecall device and then use the information to decide on a therapy. As the EP accesses the information, a notification may be sent by the server or the housecall device to the GP. In turn, the GP may be updated as to the patient's condition via the server (e.g., via an Internet connection, etc.). If appropriate, the GP may intervene or advise the EP or contact the HF for a more in-depth analysis of the patient's condition.

An exemplary method includes setting a trigger, transmitting the trigger to a computing device in a patient environment, acquiring information in the patient environment using the computing device where the information comprises data from an implantable device, analyzing the information with respect to the trigger and deciding whether to transmit information via a network to a clinical environment based on the analyzing. For example, the setting may occur in any of a variety of manners as discussed with respect to FIGS. 5, 13 and 14, as well as FIGS. 29-45, as appropriate.

A trigger may be part of a trigger table and generally includes at least one trigger parameter, which may have a numeric and/or alphanumeric value. As described with respect to FIG. 6, trigger parameters may include one or more of the following: condition parameters, numeric criterion parameters, alert level parameters, destination parameters, permission parameters, message parameters and query logic parameters. With respect to numeric criterion parameters, these may include one or more numeric values. An analysis of data from an implantable device may include use of one or more numeric criterion parameters. For example, a numeric value representative of impedance may be compared to impedance data from an implantable device. Similarly, heart rate, time, etc., may be numeric values. For time, an analysis may compare data representing an interval associated with cardiodynamics to the numeric value. For example, a pacing device may measure a PR interval, which an analysis may compare to a trigger value.

An exemplary method may include presenting a query in a patient environment using a computing device. Further, such a method may include receiving an answer to the query, optionally where deciding to transmit information depends at least in part on the answer. An analysis may include presenting a query in a patient environment using a computing device.

As already mentioned with respect to FIG. 5, acquisition of information may occur according to an event, a schedule, etc. Various examples include repeating acquisition of information if a decisions step decides not to transmit information (e.g., to a clinical environment). After acquisition, analysis may occur or analysis may occur after a certain number of acquisitions, etc.

While not shown in FIG. 5, if the trigger causes transmission of information, the method may repeat setting the trigger, especially if the transmitted information is germane to any conditions related to the trigger (e.g., patient conditions, device conditions, etc.).

As mentioned with respect to the table 505 of FIG. 6, a trigger may include an associated alert level or alert levels (e.g., based on an error or other analysis of data from an implantable device); an alert level may accompany transmission of information (e.g., to a clinician or clinical environment). Thus, a trigger may provide an alert level or alert levels, as appropriate.

A trigger may provide an address for a transmission. For example, where a decision occurs to transmit information via a network to a clinical environment, a trigger may provide an address for the clinical environment.

Where a decision occurs to transmit information via a network to a clinical environment, a condition indicator may accompany the transmission. A trigger may provide such a condition indicator.

Where a decision occurs to transmit information via a network to a clinical environment, a text message or voice message may accompany the transmission. A trigger may provide the text message or voice message. For example, the message column in the table 505 may include a text message and/or a voice message (e.g., a .wav file or other audio file). Further, a computing device may include text-to-speech or speech-to-text capabilities. Such capabilities are useful for patients that lack text entry ability or conversely speech ability. Such capabilities are useful for clinicians, for example, depending on task, etc. Further, a clinician may select a voice, an accent, a language, etc., for delivery of a message or query to a patient. For example, a clinician may select to be the speaker and to record her voice in one or more digital audio files according to a standard or a custom query, alert, command, reminder, etc. A clinician's user interface may provide for such options. Digital audio files may be stored at any of a variety of locations in the a system (e.g., housecall, implantable device, server, telephonic device, PDA, etc.).

Various exemplary methods include confirmation or security features. For example, where a decision occurs to transmit information via a network to a clinical environment, in the instance the transmission to the clinical environment fails, the deciding decides to transmit information to an alternative clinical environment or location. A trigger may provide an address for an alternative clinical environment in the instance the transmission to primary clinical environment fails.

An exemplary method may include acquiring information from more than one implantable device. An exemplary method may include acquiring information from one or more external devices. An external device may be a diagnostic instrument (e.g., blood pressure instruments, blood glucose instruments, blood gas concentration instruments, body mass instruments, body activity instruments, positive airway pressure instruments, kidney dialysis instruments, etc.).

An exemplary method may include acquiring information using a local area network associated with a patient environment and/or a wireless network associated with a patient environment. As already mentioned a patient environment may be a house, an apartment, a vehicle, etc.

A computing device in a patient environment may use cell phone circuitry for communication via a cellular phone network. Transmission of information to a clinical environment may occur via a cellular phone network. A patient environment may include access to a cable service provider network.

Transmission of information to one or more alternative locations to ensure proper receipt of information may occur automatically or in response to an event (or lack thereof). For example, an exemplary method includes deciding whether a transmission succeeded. An exemplary method may include transmitting a response from a computing device in a clinical environment to a computing device in a patient environment. Such a response may indicate that a transmission was successful or that other action should occur. Such a transmission to a patient environment may, for example, initiate a query according to query logic associated with a trigger. Such a transmission may be an alert to alert a patient where a method may include issuing the alert by a computing device in the patient environment. The computing device in the patient environment may request a response after issuing the alert to acknowledge the alert.

As already mentioned, permissions may be used to restrict access to or ability to alter information. For example, an exemplary method may include restricting setting of a trigger or altering a trigger based on one or more permissions. Such permissions may correspond to a clinical environment or clinicians in a clinical environment.

An exemplary method includes acquiring information in a patient environment using a computing device wherein the information includes data from an implantable device, presenting a query using the computing device, receiving an answer to the query via the computing device and deciding whether to transmit information via a network to a clinical environment based at least in part on the answer. Such a method may present one or more additional queries, for example, based on one or more answers. Such a method may include analyzing the acquired information and presenting the query based at least in part on the analyzing. As already discussed, a trigger may provide a query or query logic. An analysis of information may occur with respect to a trigger and a decision to present a query may occur based on such an analysis.

As discussed herein various exemplary methods, in part or in whole, may be implemented using one or more computer-readable media that include processor-executable instructions for performing various actions.

Hardware Concepts

FIGS. 15-28 show various exemplary housecall devices. Such devices typically include components of the housecall device 401 and may include other components. A housecall device may have a hand-holdable, wearable, table-top, wall-mounted, shelf-mounted or other configuration. Some of the housecall devices of FIGS. 15-28 include a base unit and a receiver unit or a satellite receiver unit, which may also transmit information. In general, a receiver unit includes circuitry to receive information from an implantable device, whether implanted or not implanted in a patient. A conventional implantable device programmer typically includes a wand and circuitry for wireless communication with an implantable device. The receiver units of the housecall devices of FIGS. 15-28 operate wirelessly and may do so using similar circuitry.

Figure 15:
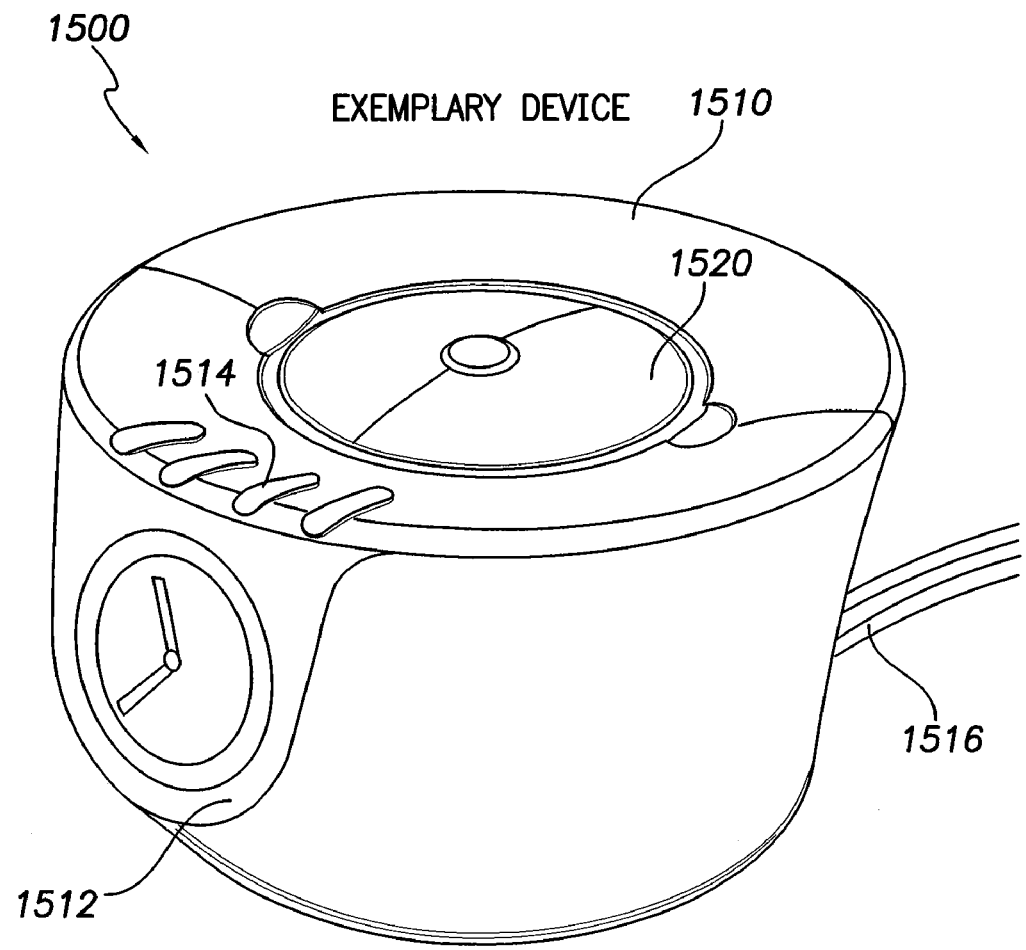
FIG. 15 is a perspective view of an exemplary housecall device for table-top use.

FIG. 15 shows an exemplary housecall device 1500 that includes a base unit 1510 and a receiver unit 1520. The base unit 1510 is configured for table-top use and includes a user interface display 1512, a series of buttons 1514 and power and communication cables 1516.

Figure 16:
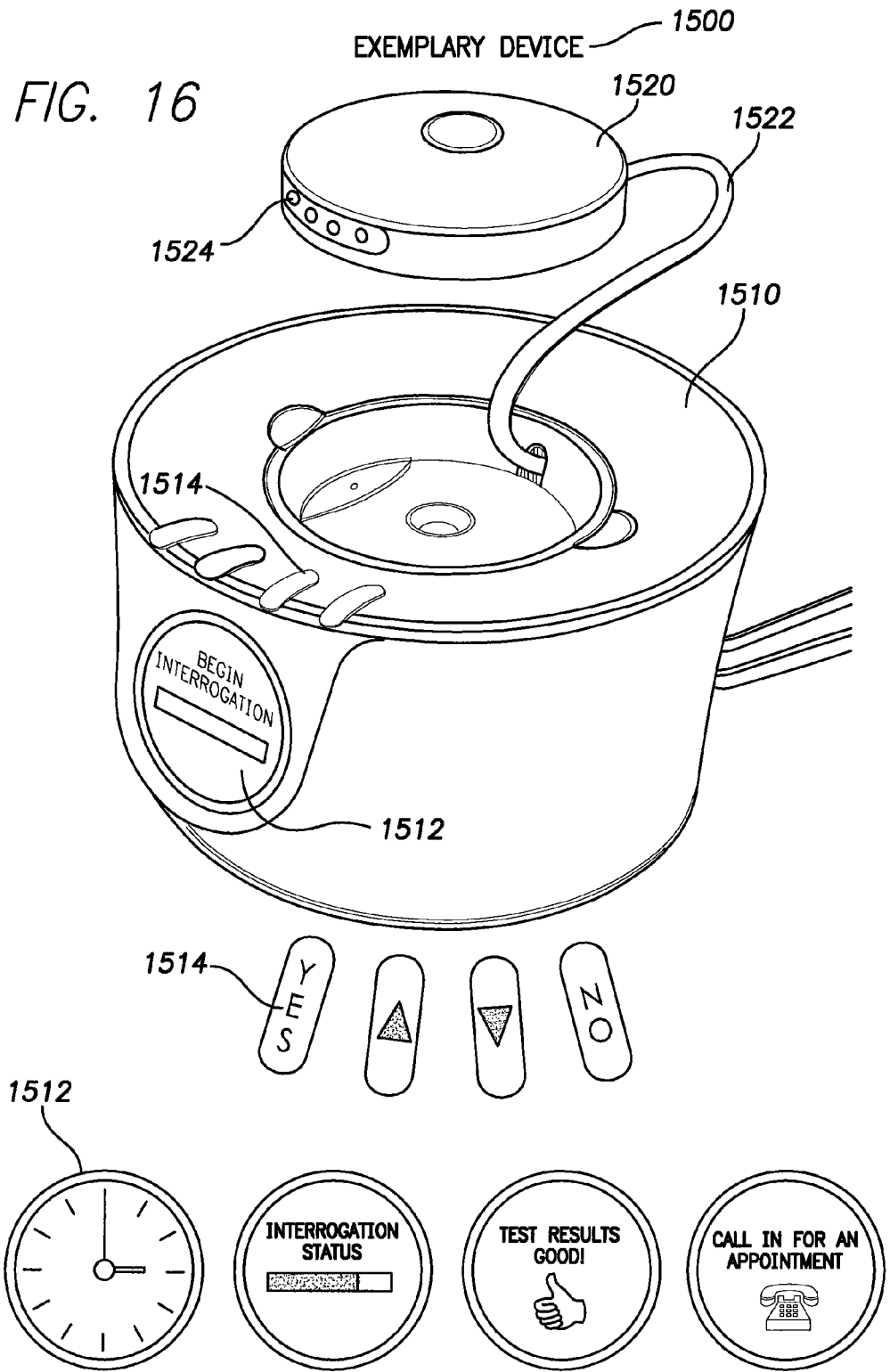
FIG. 16 is a perspective view of the exemplary housecall device of FIG. 15.

FIG. 16 shows the device 1500 of FIG. 15 with the receiver unit 1520 unseated from the base unit 1510. This illustrates how the corded receiver unit 1520 nests atop the base unit 1510. In this example, a cable 1522 connects the receiver unit 1520 to the base unit 1510, which may have a retractable cable mechanism for retracting the cable 1522. The cable 1522 provides for communication between the receiver unit 1520 and the base unit 1510 and provides power to the receiver unit 1520. A series of lights 1524 on the receiver unit 1520 optionally indicate signal strength for communication with an implantable device. The lights 1524 may also indicate status of communication.

The buttons 1514 of the base unit 1510 allow a user to browse a menu or otherwise interact with the device 1500. The buttons 1514 allow a user to interact with the user interface display 1512, which may display time, interrogation status, test results, appointment information, etc. Referring to the device 401 of FIG. 3, the user interface module 406 may provide for such display and the user interface module may be programmable by a user or by a clinician.

The device 1500 may include an AC line cord and RJ11 phone cable, PCMCIA card functionality for integrating various other connectivity technologies such as Bluetooth integration with external monitoring devices, WiFi connectivity to existing DSL/Cable broadband connection, GSM/3G cellular modem, etc. The device 1500 may include battery backup and continual connection support for automatic and regular uploading to a network that provides for clinician review without patient involvement.

Figure 17:
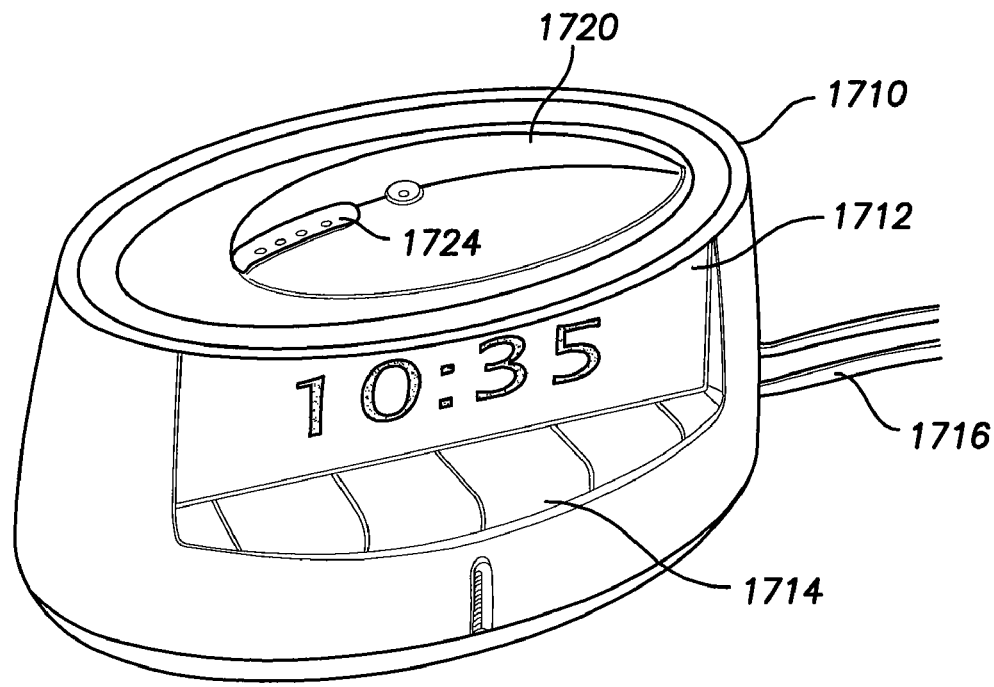
FIG. 17 is a perspective view of another exemplary housecall device for table-top use.

FIG. 17 shows an exemplary housecall device 1700 that includes a base unit 1710 and a receiver unit 1720. The receiver unit 1720 nests in a socket atop the base unit 1710 and includes a series of lights 1724 for conveying information to a user. The base unit 1710 includes a user interface display 1712 and power and communication cables 1716. While two cables are shown, the device 1700 may also include wireless communication capabilities. For example, the base unit 1710 may be able to communicate via cable (e.g., standard phone, Internet, etc.) and wirelessly (e.g., cell phone, Bluetooth, WiFi, etc.). In an alternative, the device 1700 communicates wirelessly with a network and may have only a single cable for power.

The device 1700 may include a speaker for audible signals or voice communication with a user. Various types of information may be displayed via the display 1712. For example, a health related message appears in the user interface display 1712', a transmission related message appears in the user interface display 1712" and an appointment related message appears in the user interface display 1712'". Buttons on the base unit 1714 allow a user to respond to questions posed in the display 1712 or to navigate a menu for other actions. Large sized buttons and display can facilitate use for patients that may have motion or sight impairment.

Figure 18:
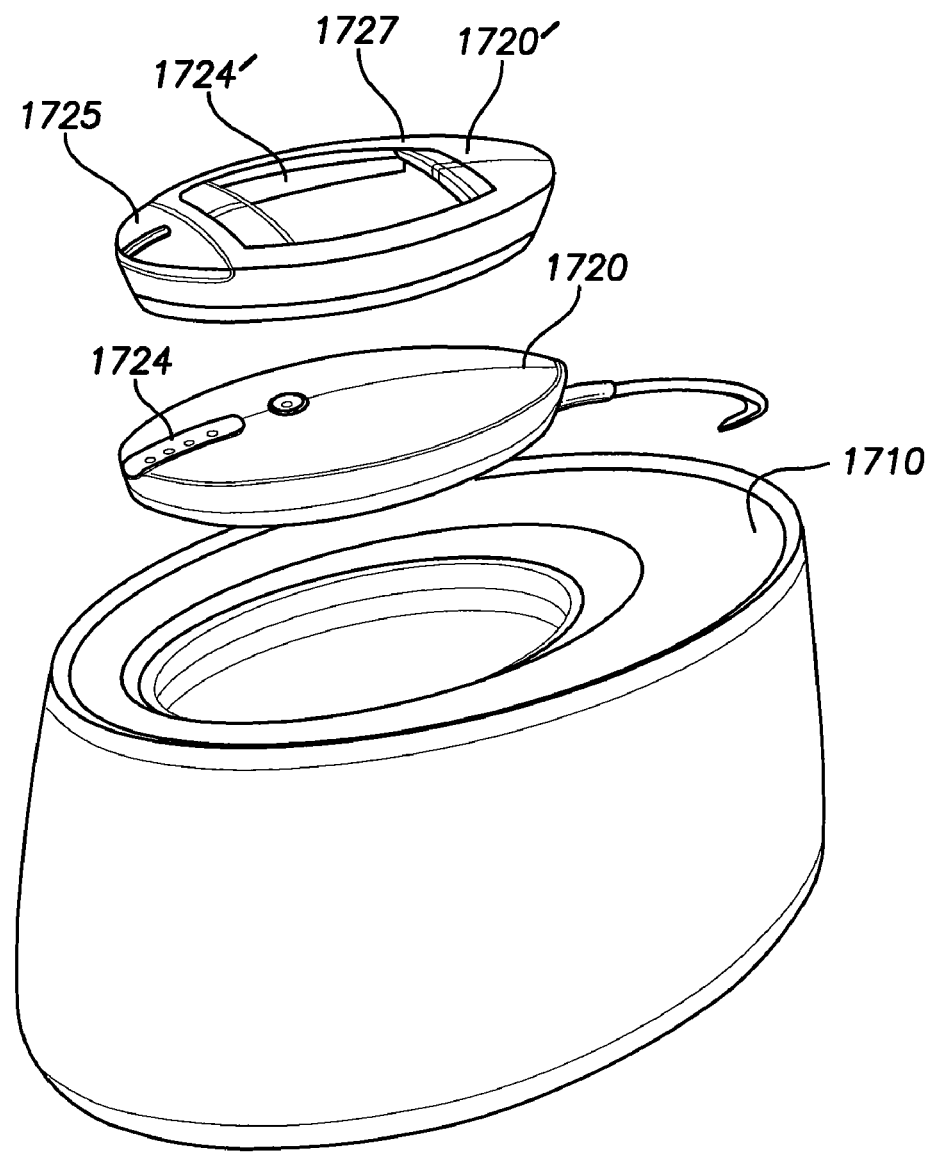
FIG. 18 is a perspective view of an exemplary housecall device for table-top use with two options for receiver units.

FIG. 18 shows several variations of the device 1700. For example, a user interface display 1724 may be on the receiver unit 1720' instead of the base unit 1710. An exemplary housecall device may include a base unit and a receiver unit where each includes a user interface display. In FIG. 18, the receiver unit 1720' also includes two sets of buttons 1725, 1727 for responding to information presented on the display 1724 and for navigating a menu or other options. The receiver unit 1720 or the receiver unit 1720' may nest in a socket in the base unit 1710.

Figure 19:
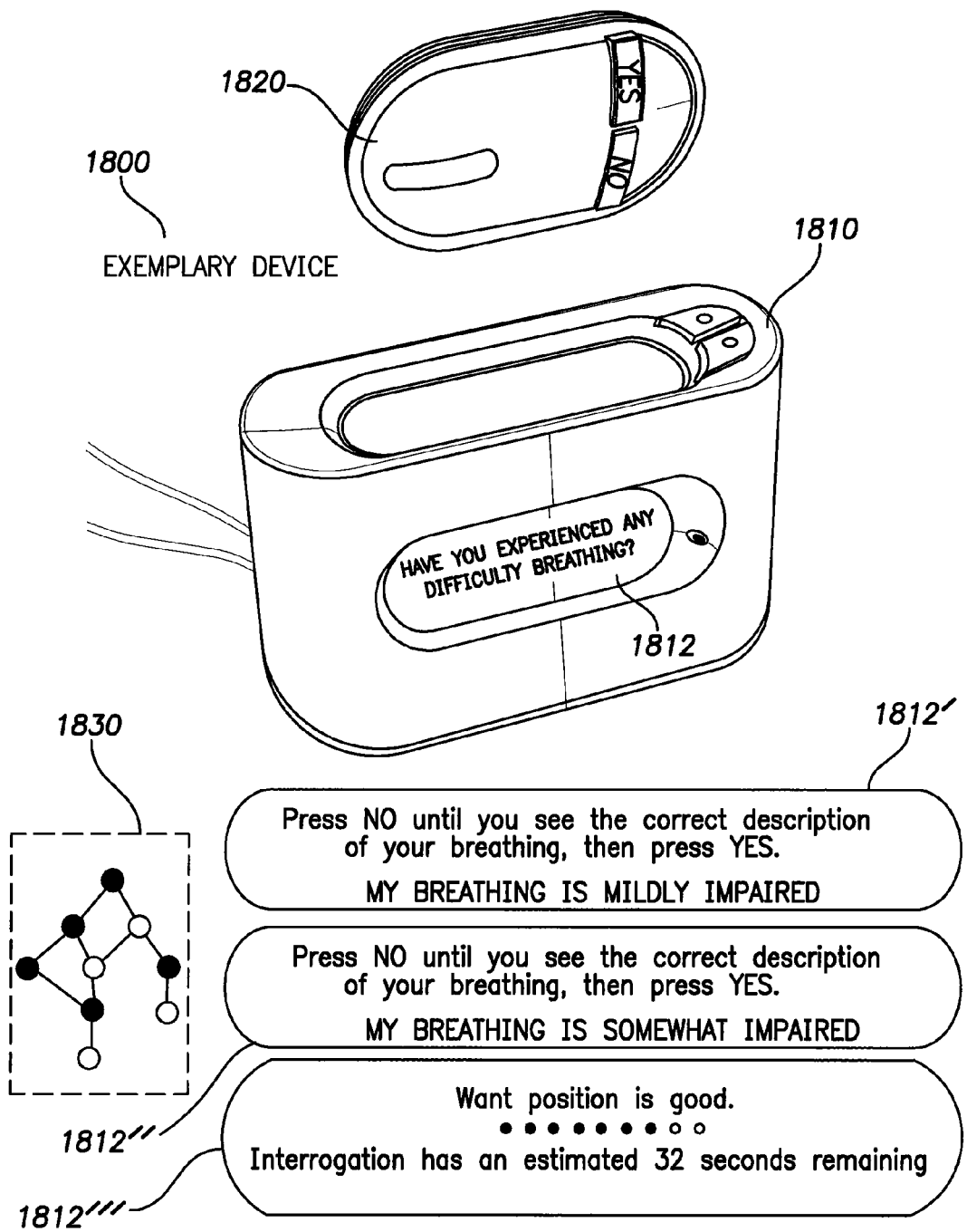
FIG. 19 is a perspective view of an exemplary housecall device for table-top use.

FIG. 19 shows an exemplary housecall device 1800 that includes a base unit 1810 and a receiver unit 1820. The base unit 1810 includes a user interface display 1812 that can display various information to a user. The displays 1812' and 1812" display health related questionnaires and the display 1812'" displays transmission and interrogation information where the receiver unit 1820 is referred to as a wand.

The device 1800 includes query logic 1830 for use in presenting information to a patient or other care provider. For example, based on a particular condition or event, the query logic 1830 may call for a certain query deliverable via a code, a text message, a voice message, etc. In turn, an answer may be provided to the query (e.g., voice, text, etc.). Once provided with an answer, the query logic 1830 may present another query and so on until sufficient information is acquired. The device 1800 may use the query logic 1830 in making a decision, for example, as to transmission of information or an alert and/or as to location of such a transmission. The exemplary query logic 1830 may use one or more triggers and a trigger may call for use of a query or query logic. For example, in the table 505, the column QL may indicate query logic for a trigger.

Figure 20:
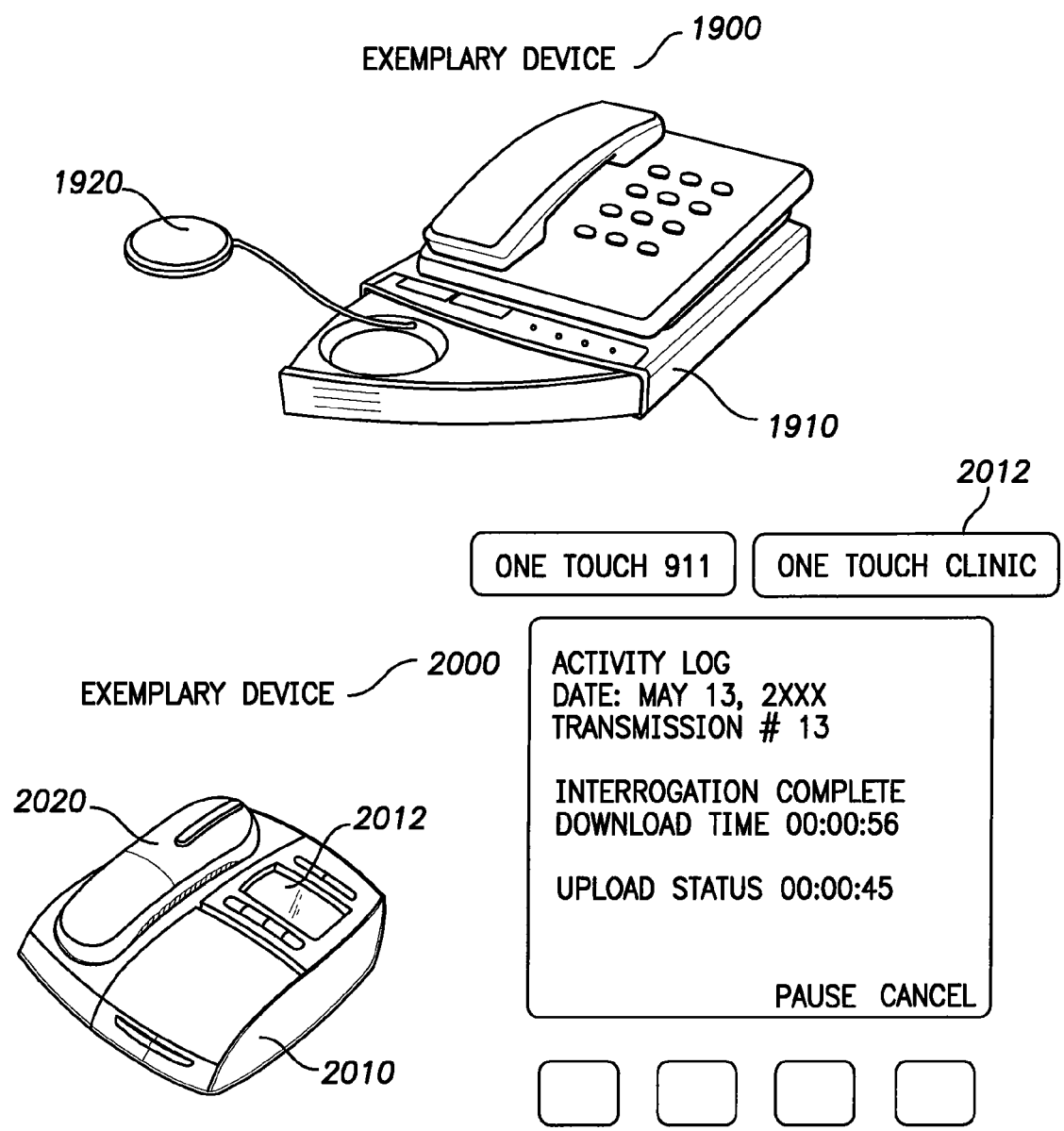
FIG. 20 is a series of perspective views for two exemplary housecall devices that interact with telephones.

FIG. 20 shows two exemplary, phone-based housecall devices 1900, 2000. The housecall device 1900 includes a base unit 1910 that cooperates with a conventional telephone. For example, a cable may connect the base unit 1910 with a conventional telephone. The base unit 1910 includes a swing out drawer that seats and stores the receiver unit 1920, which may be connected to the base unit 1910 by a cable. Alternatively, the receiver unit 1920 communicates with the base unit 1910 wirelessly. The base unit 1920 may also serve to charge a battery of the receiver unit 1920 where a cable is not used to connect the base unit 1910 and the receiver unit 1920.

The exemplary housecall device 2000 includes a base unit 2010 with integrated telephone circuitry for operating a conventional wired or wireless handset 2020 that also serves as a receiver unit. The base unit 2010 includes a user interface 2012 with a display and various buttons. The display may present information germane to communications, health, device condition, etc. In this example, the user interface 2012 includes a one touch "911" emergency button and a one touch clinic call button. Buttons to pause or cancel a communication or transmission are also included.

In an alternative configuration, the device 2000 includes a conventional wired or wireless handset and a receiver unit stored in a compartment of the base unit 2010.

Figure 21:
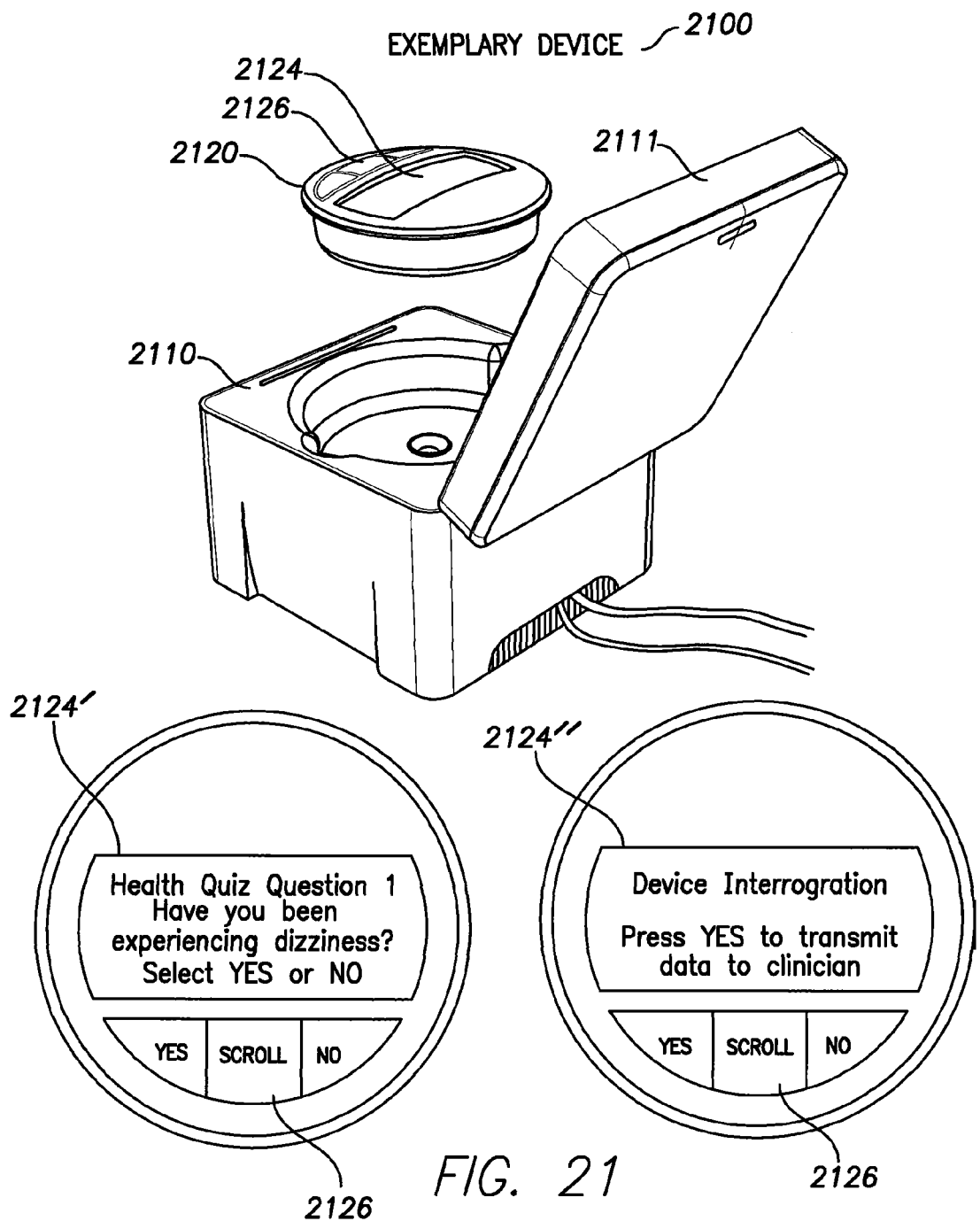
FIG. 21 is a perspective view of an exemplary housecall device for table-top use that includes a receiver unit with a user interface display.

FIG. 21 shows an exemplary housecall device 2100 that includes a base unit 2110 and a receiver unit 2120. In this example, the receiver unit 2120 includes a user interface display 2124 and a series of buttons 2126 for responding to information presented by the display 2124 and for navigating a menu or other options. The display 2124 may present information such as a health questionnaire 2124' or information transmission options 2124".

The base unit 2110 optionally includes a user interface display, which may be a touch screen display. For example, a lid 2111 may include a display on an inside or outside surface. Such a lid display configuration may be in addition to a receiver unit display or as an alternative to a receiver unit display.

The lid 2111 may operate according to touch, for example, a push down on the lid may cause the lid to pop-up or lockdown. The lid 2111 may include a light such as a night light to facilitate locating the device at night. The device 2100 may also include a speaker for audible communication and signals.

As shown in FIG. 21, the receiver unit 2120 nests in a socket in the base unit 2110. The base unit 2110 may provide for charging a battery of the receiver unit. Further, communication of information may occur from the receiver unit 2120 to the base unit 2110, or network connected thereto, only when the receiver unit 2120 is docked or stored in the base unit 2110. The receiver unit 2120, as various other receiver units, includes circuitry for communication with an implantable device. This circuitry may be suitable for communicating information to the base unit 2110 or other circuitry may be used for such communication or transfer of information.

The base unit 2110 includes a power cable and may include other cables for communication, etc. For example, the base unit 2110 may include a connector such as a RJ11 telephone jack.

As already mentioned, the housecall device 2100 may include a topside touchscreen where the screen becomes active when displaying reminders, alerts, or interaction status. The housecall device 2100 may include web-browser software suitable for connecting to a website and displaying a webpage. For example, a touch-screen interface may allow a user to access a clinic, a manufacturer, or a housecall device webpage. Such webpages may be designed specifically for display on the housecall device and hence have large fields and buttons for ease of use.

FIG. 22 shows an exemplary housecall device 2200, with a tablet configuration or essentially flat plane or panel configuration. The device includes a base unit 2210 that performs various functions. The base unit 2210 houses a receiver unit 2220. The base unit 2210 includes a user interface display 2212 and a lid 2214 for accessing a compartment that stores the receiver unit 2220.

The various devices 2200 may include web-browser software and for the base units 2210 and 2230, they may display webpages provided by one or more websites (e.g., device manufacturer, clinic, insurer, etc.). The devices 2200 may allow for interaction with such websites via the webpages or they may act in a passive manner (e.g., simply as a display for the webpages).

The devices 2200 may include one or more batteries that are recharged via cooperation with a docking station or a charger. The devices 2200 may also store a power cord for use in operation or charging a battery. The devices 2200 may be portable and allow for wireless communication with a network to, for example, transmit information received by any of the receiver units 2220, 2240, 2260, 2280, from an implantable device. The devices 2200 may include a port for communication such as a telephone port, a cable port, a USB port, a Firewire port, etc. Portability of the any of the housecall devices 2200 allows a user to bring the device to a clinic or other site (e.g., vacation home, hotel, boat, vehicle, etc.). For example, in a hotel, a user may connect the one of the base units 2210, 2230, 2250, 2270 to the Internet using a hotel's Internet network. Hence, the devices 2200 may optionally allow a patient to experience a more normal and unencumbered lifestyle.

The devices 2200 may include one or more speakers. The base unit 2230 may include a touch screen user interface or a base unit may include buttons and a display where the buttons at least partially surround the display, similar to an ATM configuration. For example, such a display may include specific zones (e.g., A, B, C and D), which may represent possible answers to a query.

An exemplary housecall device optionally includes one or more features of an implantable device programmer such as the Model 3510 programmer or the MERLIN™ programmer marketed by St. Jude Medical (Sylmar, Calif.). An exemplary housecall device may include circuitry and control logic to send emails, to receive emails, to send a fax, to receive a fax, to send a text message, to receive a text message, to receive an audio file (e.g., a digital audio file such as a wav. file), to send an audio file, etc.

An exemplary housecall device may be programmed to present questions randomly such that a patient does not get accustomed to a particular sequence of questions or a time of questioning. A housecall device may issue a signal until a question is answered, for example, as a reminder that a query is pending. Questions may be asked in a series over days, weeks, etc. For example, if a clinician sets the query logic to ask a series of questions within a month, the logic may present these questions in a specified order, an order determined at least in part by an answer to a question and/or in a random order. As already explained, a clinician may program query logic (see also user interface 7090 of FIG. 45).

Figure 23:
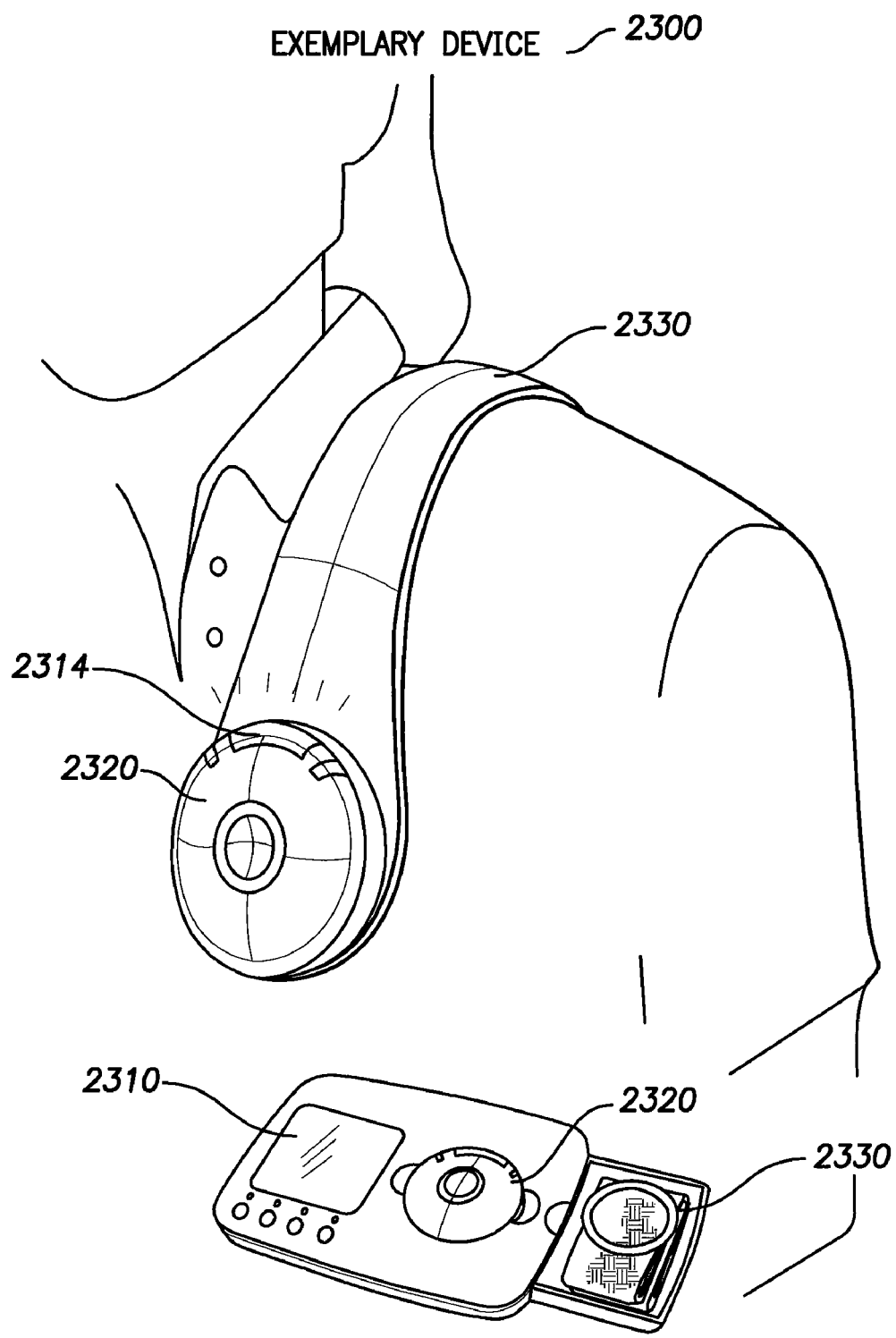
FIG. 23 is a series of perspective views of an exemplary housecall device suitable for wearing or table-top use.

FIG. 23 shows an exemplary housecall device 2300 that includes a base unit 2310 and a wearable receiver unit 2320, for example, wearable through use of a strap or holster 2330. The base unit 2310 includes a compartment accessible via a sliding tray for storing the strap 2330. The base unit 2310 also includes a socket for storing the receiver unit 2320.

When attached to the strap 2330, the receiver unit 2320 is position over the left pectoral muscle of a patient. Most implantable cardiac therapy devices are implanted in a pectoral pocket. Hence, the strap 2330 allows the receiver unit 2320 to be positioned in close proximity to an implanted device to facilitate communication. Such communication may occur on an as needed or desired basis as long as the patient is wearing the receiver unit 2320 or in close enough proximity to the receiver unit 2320 to allow for reliable communication. For example, a patient wearing a shirt with a pocket over the left pectoral muscle may place the receiver unit 2320 in the shirt pocket to thereby allow for communication with a device implanted in a pectoral pocket. Communication using the receiver unit 2320 may occur in a hands-free mode where user interaction is unnecessary.

The receiver unit 2320 includes one or more lights 2314 and may include a speaker to emit an audible signal. The receiver unit 2320 may include a vibratory mechanism, similar to those used in cell phones, to allow a wearer to receive information where visual or audible signals are not suitable (e.g., a theatre, a meeting, etc.). The one or more lights 2314 may help in positioning the strap 2330 or in notifying the wearer of transmissions, battery level, when to take medication or other action, etc.

The base unit 2310 may include various features as described with respect to other base units or housecall devices (e.g., a user interface display, buttons, a speaker, a charger for a receiver unit, one or more cables, one or more communication interfaces, etc.).

Figure 24:
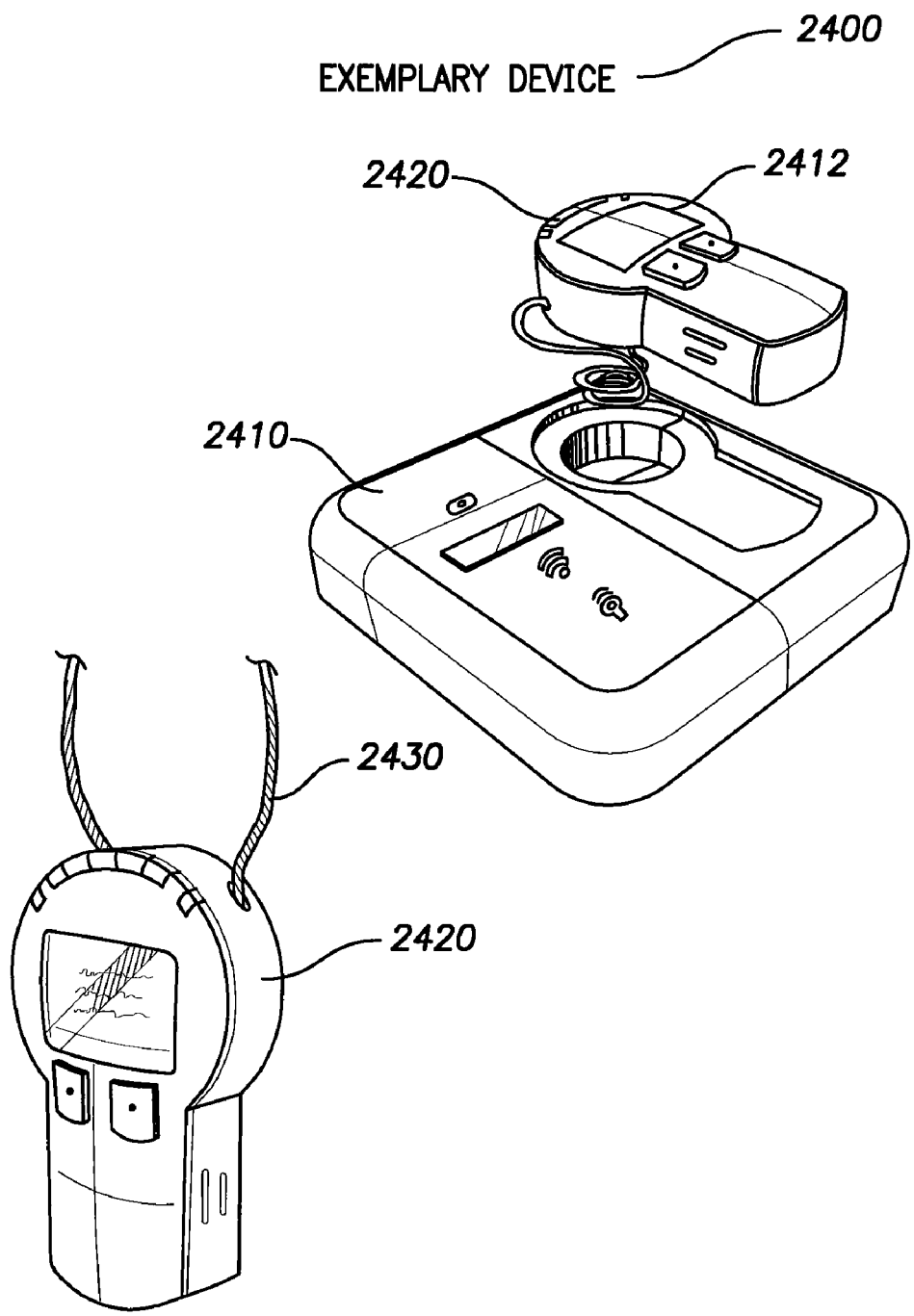
FIG. 24 is a series of perspective views of another exemplary housecall device suitable for wearing or table-top use.

FIG. 24 shows an exemplary housecall device 2400 that includes a base unit 2410 and a receiver unit 2420. A strap 2430 attaches to the receiver unit 2420 to thereby allow a user to wear the receiver unit 2420. In this example, the receiver unit 2420 is battery powered where the base unit 2410 provides for charging the battery. The receiver unit 2420 includes a user interface display 2412 for displaying various information to a user. The base unit 2410 may include a user interface display as well.

The receiver unit 2420 may provide for communication with an implantable device and for communication with a network. Alternatively, the base unit 2410 may provide for communication with a network. Communication with a network may occur using a wired communication interface or a wireless communication interface.

The base unit 2410 may additionally act as a hub to receive information from one or more sources other than the receiver unit 2420 (e.g., a weight scale, a blood pressure monitor, a pedometer, etc.). Alternatively, the receiver unit 2420 may additional act to receive information from one or more sources other than an implantable device (e.g., a weight scale, a blood pressure monitor, a pedometer, etc.).

The base unit 2410 may operate as a wireless base unit for connecting a variety of devices and for transmitting information received from such devices to a computer or a computer network. The base unit 2410 may operate in conjunction with a conventional wireless base unit such as a base unit commonly used for a home network (e.g., WiFi, Bluetooth, etc.).

The base unit 2410 may include circuitry for locating the receiver unit 2420. For example, a user may push a button on the base unit 2410 that causes the receiver unit to issue an audible signal, a visible signal, etc.

Figure 25:
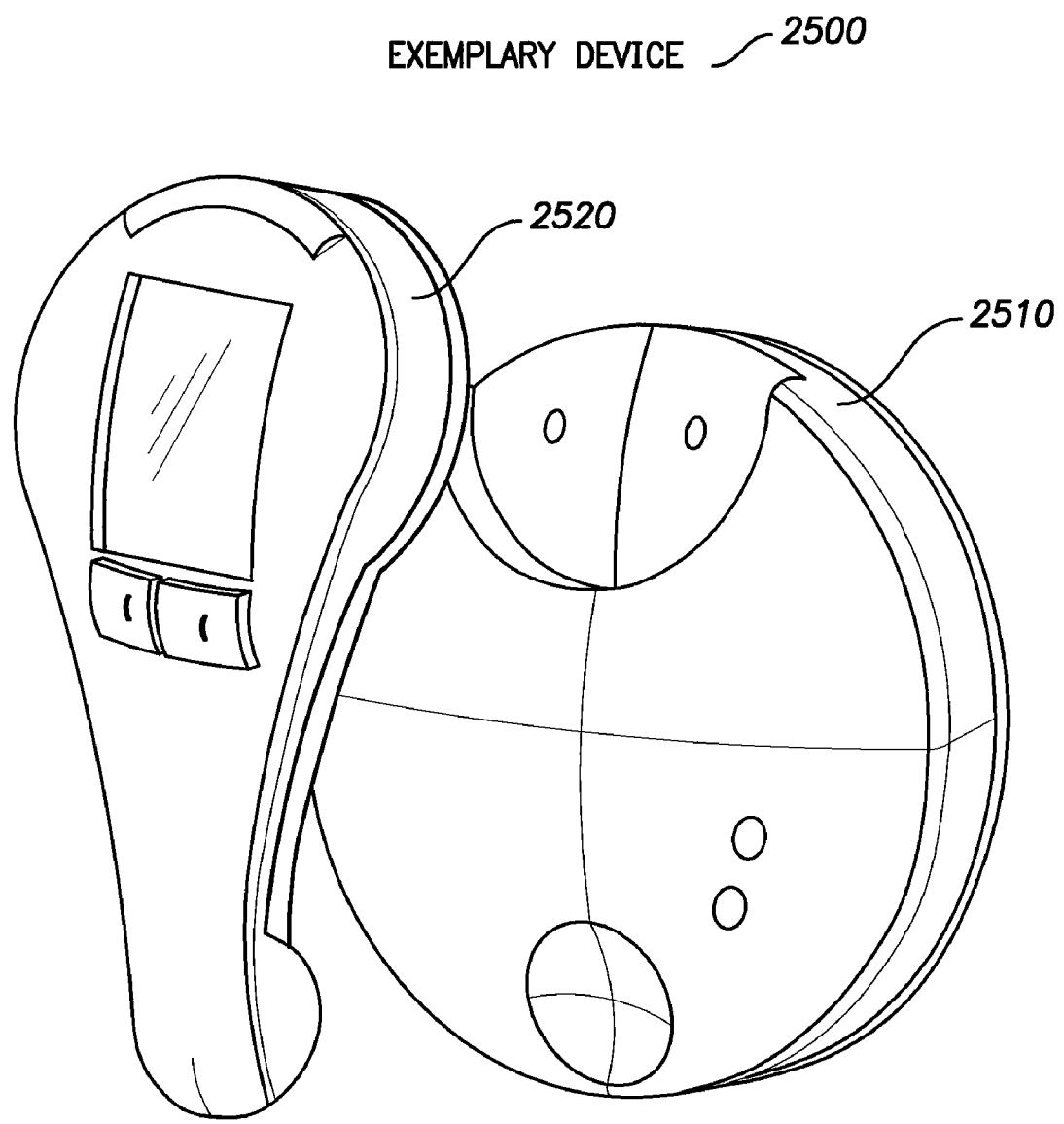
FIG. 25 is a perspective view of an exemplary housecall device suitable docking on a wall mounted base.

FIG. 25 shows an exemplary housecall device 2500 that includes a base unit 2510 and a receiver unit 2520. In this example, the base unit 2510 mounts to a wall and acts as a hook to hang the receiver unit 2520. The base unit 2510 may connect to a power supply and optionally to a network such as a telephone or computer network. The base unit 2510 may act as a charger to charge a battery of the receiver unit 2520. The receiver unit 2520 may operate as a telephone handset in addition to operating as a receiver for communicating with an implantable device.

The receiver unit 2520 may include various user interfaces such as a display, lights, buttons, a vibratory mechanism, a speaker, etc. The housecall device 2500 optionally includes a holster that allows a user to carry the receiver unit 2520. Alternatively, the receiver unit 2520 includes a clip that allows a user to clip the unit to a belt, a strap, etc.

The device 2500 may be suitable for use in a secondary or smaller clinic or in a public place such as on a plane, in an airport, etc. The device 2500 may be capable of communicating with a variety of implantable devices from a variety of manufacturers. In general, the device 2500 would be able to acquire basic information as to the type of implantable device and set operational mode(s). In emergency situations, such basic information may be provided to those first on a scene or to better prepare those that may have access to equipment related to the particular implantable device.

Figure 26:
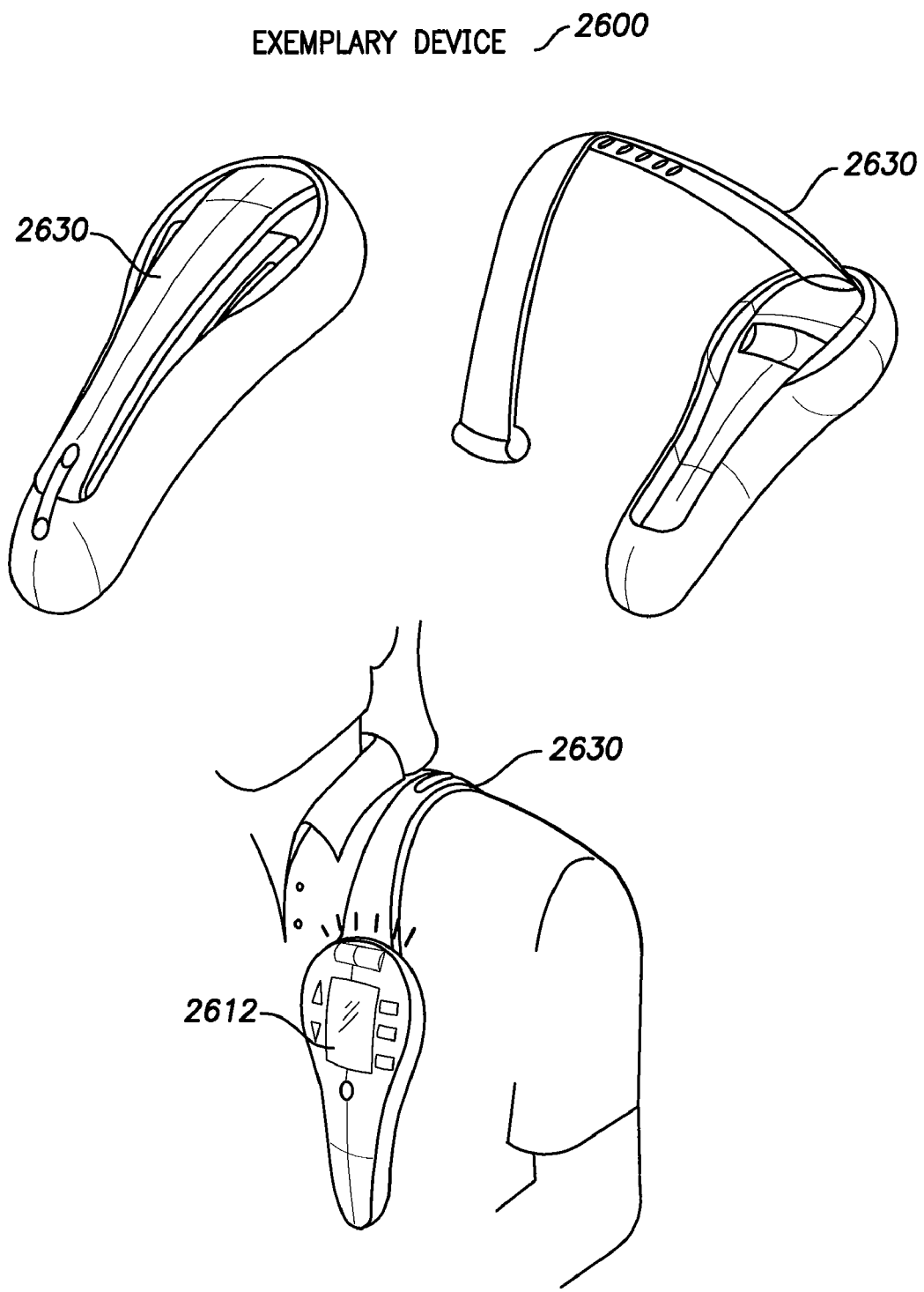
FIG. 26 is a series of perspective views of an exemplary housecall device suitable for wearing.

FIG. 26 shows an exemplary housecall device 2600 that includes a compartment for storing a strap 2630. In this example, the strap 2630 folds for storage in the compartment of the housecall device 2600. The strap 2530 allows for positioning of the device in close proximity to an implanted device implanted in a pectoral pocket. The device 2600 includes one or more user interfaces such as a display 2612. The device 2600 optionally includes one or more communication ports for wired or wireless communication with a network. The device 2600 includes one or more batteries that are replaceable or rechargeable using a separate charging device or a built-in recharger that connects to a power outlet via a power cord and optionally a transformer.

Figure 27:
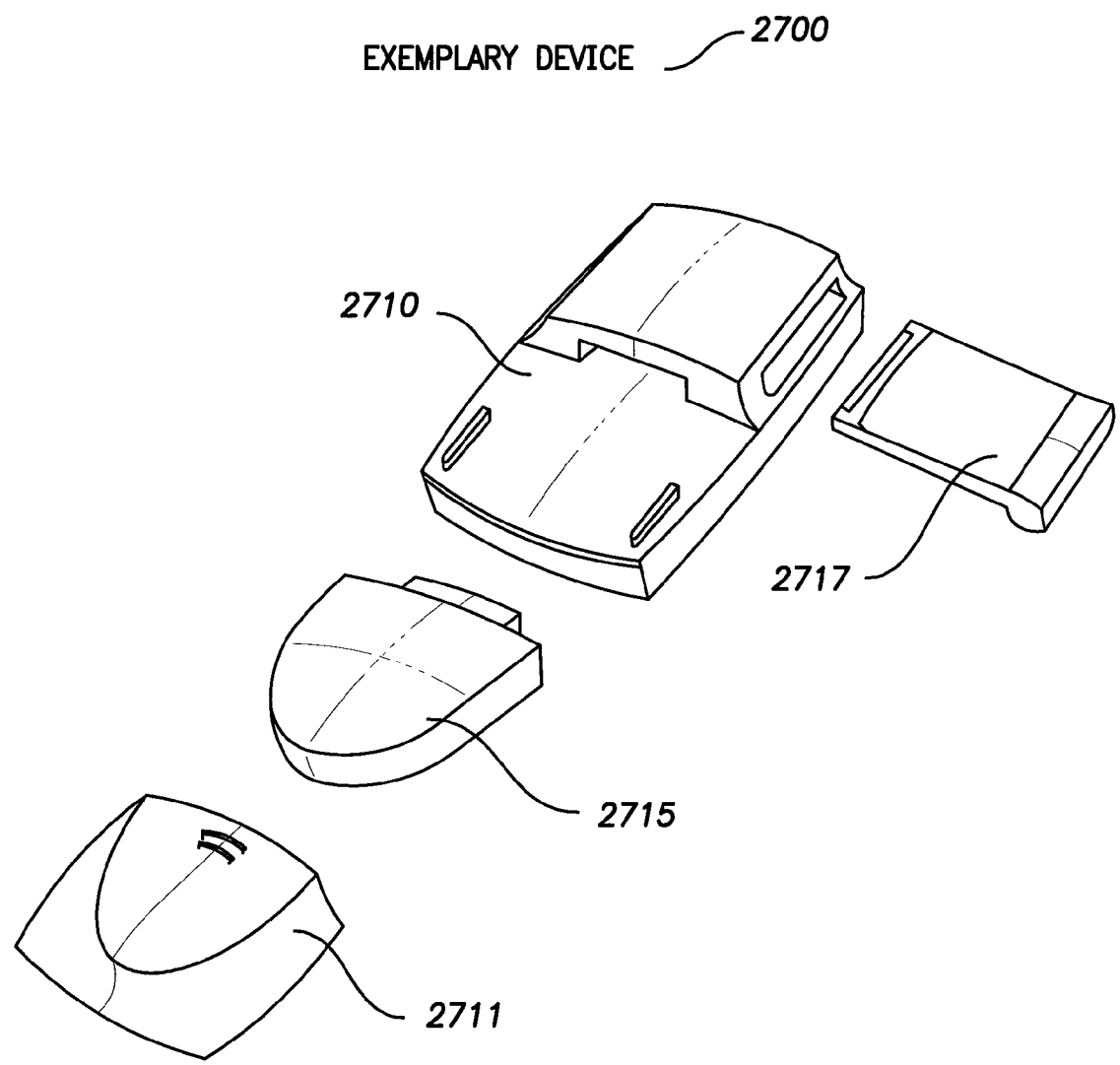
FIG. 27 is an exploded perspective view of an exemplary housecall device configured for hand held operation.

FIG. 27 shows an exemplary device 2700 in a partially exploded view to illustrate various components and functionality between components. The device 2700 has a hand-holdable configuration similar to a palm style personal data assistant (PDA). The device 2700 includes a base component 2710, a battery or other module 2715 and a cover 2711. The base component 2710 includes a slot for receipt of a communication card 2717 or other card (e.g., PCMCIA card). The device 2700 includes circuitry for communicating with an implantable device and for communicating with a network or a computer connected to a network. Such circuitry may be at least partially within the card 2717. The device 2700 may include software for communication with a computer network and for accessing website and displaying webpages.

The device 2700 may include a wireless or other RF like module or a wired module (e.g., provided by the card 2717 or the module 2715). Thus, the base 2710 may provide for various options that can be tailored based on costs, patient needs, etc.

Figure 28:
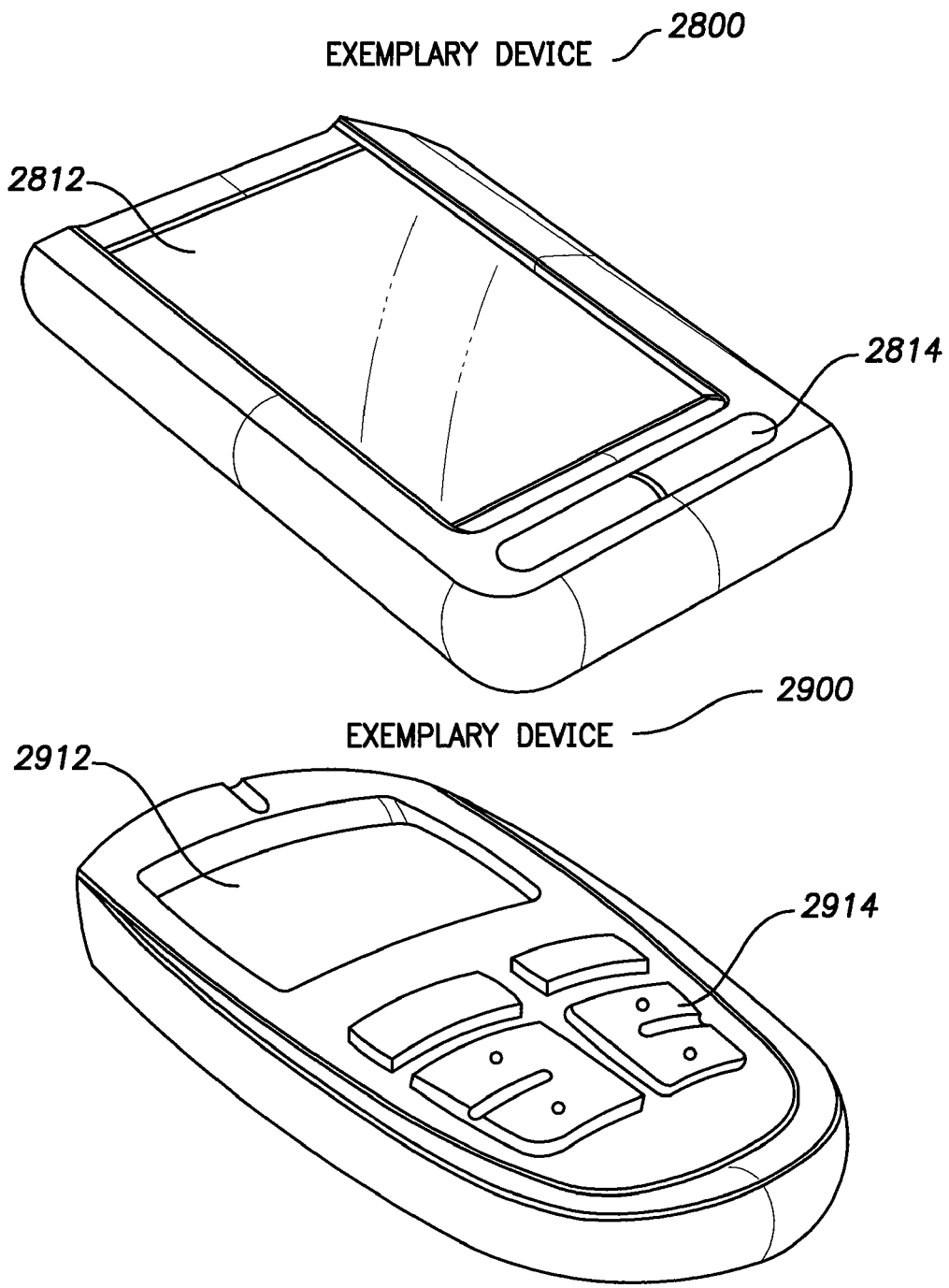
FIG. 28 is a series of perspective views of two exemplary housecall devices configured for hand held operation.

FIG. 28 shows exemplary housecall devices 2800 and 2900 that may include one or more features of the device 2700, or other housecall devices. The device 2800 includes a user interface display 2812 and one or more buttons 2814. The device 2900 also includes a user interface display 2912 and one or more buttons 2914. The displays 2812 and 2912 are optionally touch-screen displays. The devices 2800 and 2900 may include circuitry such as that found in a cell phone for connection to a telephone network or other network. The devices 2800 and 2900 may include circuitry for communication with devices such as a weight scale, a blood pressure monitor, a pedometer, etc.

The devices 2800 and 2900 may be assigned telephone numbers or network addresses (e.g., one or more URLs). Such features can allow a service provider to contact a patient or to communicate with the device 2800 or 2900 on an as needed or desired basis. For example, a service provider may desire to upgrade software on the device 2800. Such an upgrade may occur without bothering the user where a cell phone number exists for the device 2800 specifically for device operations. In this example, the device 2800 may have another phone number for voice or user notification operations. Where a device has a single address or "silent" phone number, an instruction or signal may be communicated to the device to thereby cause the device to notify a user (e.g., audible signal and visual display of a clinician's phone number).

A clinician or other service provider may use a device such as the device 2800 or the device 2900 when visiting a patient in a clinic, at home or in a business office. For example, an insurer may use such a device to interrogate an implanted device for treatment parameters, a treatment schedule, or other information.

Various exemplary devices aim to be acceptable for a patient and a patient's home environment. In particular, a patient may be more willing to use a device that looks like an ordinary alarm clock or clock radio as opposed to a device that looks like something from an acute care clinic. Thus, various devices can operate as clocks, telephones, or other innocuous objects. Further, when a device includes an ordinary utilitarian function, then a user is more likely to interact with the device or place the device in plain view.

Various devices may be based on a personal computer (e.g., laptop or desktop), as many homes include personal computers. A personal computer may operate as a base and a unit may include circuitry for communication with an implantable device. In such an arrangement, the computer may perform most or all of the processing. In the former, the unit may include a processor and memory while in the latter, the unit may include basic communication circuitry.

An exemplary device may operate according to an existing network protocol. For example, smart home systems on a home network may operate according to a protocol and an exemplary device may use this protocol for communication and then use particular software for other procedures (e.g., interrogation, processing, etc.). An existing communication system for home appliances or other equipment (e.g., health, exercise, etc.) may provide application programming interfaces (APIs) or other features that allow for interoperability, plug-n-play, etc. Thus, an existing architecture may provide for at least a communication base for an exemplary device. Further, such an architecture may provide computer user interfaces that may reduce programming requirements (e.g., consider use of standard forms provided by general database applications).

An exemplary device includes a processor, one or more communication interfaces, memory and one or more modules stored in the memory that include processor executable instructions to receive data from an implantable device via at least one of the one or more communication interfaces, to interrogate the data for one or more particular types of data, to process one or more particular types of data and to transmit information via at least one of the one or more communication interfaces. For example, the device 201 of FIG. 2A and the devices of FIG. 3 include one or more of these features.

With respect to types of data, data received from an implantable device may include at least one type of data such as therapy data, patient condition data and device condition data. For example, data received from an implantable device may include therapy data for a cardiac pacing therapy and may further include data for one or more cardiac pacing parameters (e.g., parameter values, parameter values with respect to time, etc.).

The aforementioned exemplary device may transmit information in the form of a query. For example, one or more modules may include processor executable instructions to present the query via one of the one or more communication interfaces. Further, one or more modules may include processor executable instructions to receive an answer to the query via one of the one or more communication interfaces. Yet further, one or more modules may include processor executable instructions to transmit information based at least in part on the answer via one of the one or more communication interfaces.

As already mentioned (see, e.g., FIG. 1), an exemplary device may include one or more modules stored in memory that include processor executable instructions to receive information from a diagnostic instrument via at least one of the one or more communication interfaces. Such diagnostic equipment may include a blood pressure instrument, a blood glucose instrument, a blood gas concentration instrument, body mass instrument (e.g., a scale), a body activity instrument, a positive airway pressure instrument (e.g., for treatment of apnea), a kidney dialysis instrument, etc. An exemplary device may include one or more modules with processor executable instructions to interrogate the information from a diagnostic instrument for one or more particular types of information and to process such information. Such a device may include processor executable instructions to process information from a diagnostic instrument and information from an implantable device.

As already mentioned, a decision to transmit information may occur (see, e.g., FIG. 5). An exemplary device may make a decision to transmit information via at least one communication interface where the decision depends at least in part on processing of data received from an implantable device and/or depends at least in part on interrogation of data received from an implantable device. A decision may rely on a trigger, hence, a device may include one or more triggers for use in deciding whether to transmit information via at least one communication interface.

An exemplary device may receive information from a clinician via any of a variety of communication paths. For example, a device may include one or more modules with processor executable instructions to receive information from a clinician via at least one communication interface. Such clinician provided information may be used in deciding whether to transmit information via at least one communication interface. Such clinician provided information may be used to present a query via at least one communication interface.

With respect to communication interfaces, a device may include a speaker, a microphone, one or more keys, a vibrating mechanism (e.g., when in contact with a patient's body or other care provider's body), a wireless interface, a network interface, telephone interface, etc.

As already described an exemplary device may include a handheld unit, which includes a communication interface, and a base. The communication interface of the handheld unit may be a wireless communication interface for wireless communication with the base. A base may include a docking mechanism for the handheld unit. The handheld unit may include one or more lights to convey information to a user. Such information may indicate quality of communication information, end of communication information, etc.

An exemplary device may receive data from an implantable device via at least one communication interface responsive to a user positioning the handheld unit proximate to the implantable device. For example, when a user positions the device (e.g., a handheld unit or wearable device) proximate to an implantable device, communication may be established or initiated by any of a variety of techniques (e.g., the external device may transmits a signal that requires a certain proximity to the implantable device for receipt).

An exemplary device may include one or more mechanisms (e.g., user inputs or communication channels) that initiate receipt of data from an implantable device via at least one communication interface. Such a mechanism may rely on a voice command, a button, etc.

Various exemplary devices include a mount, for example, to mount the device to a communication outlet (see, e.g., the component 465 of FIG. 4). Such an outlet may be a phone outlet, a network outlet, etc.

An exemplary device may be a personal computer. In such an example, the personal computer would include a handheld unit for positioning proximate to an implantable device. Alternatively, a wireless home network may provide a signal range that covers a portion of the home, the entire home, the yard, etc. Such a wireless home network may also provide for communication with one or more other instruments (e.g., diagnostic instruments, home appliances, etc.). As part of a therapy, a clinician may prescribe a certain home temperature or a temperature that varies with respect to some patient condition. In this example, the device may receive information regarding the patient condition and then instruct the home heating/cooling system to adjust the environment (e.g., temperature, humidity, etc.). As already mentioned, a device may communicate with a positive airway pressure instrument for use in treating apnea (e.g., sleep apnea). A device may use a communication interface for a home network or other communication interface for communicating with such an apnea treatment instrument.

As shown in various figures, a device may include a clock to display time to a user. Such a clock may also be used in timing one or more events (e.g., alerts, data acquisition, data transmission, etc.). A device may include an alarm to alarm a user. In another example, an exemplary device includes telephone circuitry such as cell phone circuitry. Such a device may communicate via telephone networks for data and/or voice transmissions. An exemplary device may include an Internet browser module for use in browsing the Internet. Such a module is typically software-based. A device with telephone circuitry may include browser software for browsing a network such as the Internet.

An exemplary device may include harness to harness the device to a user (see, e.g., FIGS. 23, 24, 26). Such a harness may be a shoulder harness, a neck strap, etc. A harness may help position at least one communication interface proximate to an implantable device of a user. A device may include a display (LCD, LED, etc.) to display status of an implantable device.

As described herein, various arrangements of tasks are possible, including arrangements other than those of FIGS. 2A and 2B. An exemplary system includes a first computing device with a processor, one or more communication interfaces, memory and one or more modules stored in the memory that include processor executable instructions to receive data from an implantable device via at least one of the one or more communication interfaces and a second computing device that with a processor, one or more communication interfaces, memory and one or more modules stored in the memory that include processor executable instructions to receive data from the first computing device, to interrogate the data for one or more particular types of data, to process one or more particular types of data and to transmit information via at least one of the one or more communication interfaces.

In such a system the second computing device may include a wireless communication interface and/or be a handheld, wireless computing device. The first computing device typically includes processor executable instructions to transmit information via at least one communication interface. Such information may be a query that can be presented via a communication interface. Further, the first device may include one or more modules with processor executable instructions to receive an answer to the query via a communication interface (e.g., keypad, microphone, etc.). The first device may include one or more modules with processor executable instructions to transmit information, based at least in part on the answer, via a communication interface.

In another arrangement, a system includes a first computing device with a processor, one or more communication interfaces, memory and one or more modules stored in the memory where the one or more modules include processor executable instructions to receive data from an implantable device via at least one of the one or more communication interfaces and to interrogate the data for one or more particular types of data; and a second computing device with a processor, one or more communication interfaces, memory and one or more modules stored in the memory where the one or more modules include processor executable instructions to receive data from the first computing device, to process one or more particular types of data and to transmit information via at least one of the one or more communication interfaces.

As with the other arrangement, the second computing device may include a wireless communication interface and/or be a handheld, wireless computing device. The first computing device typically includes processor executable instructions to transmit information via at least one communication interface. Such information may be a query that can be presented via a communication interface. Further, the first device may include one or more modules with processor executable instructions to receive an answer to the query via a communication interface (e.g., keypad, microphone, etc.). The first device may include one or more modules with processor executable instructions to transmit information, based at least in part on the answer, via a communication interface.

FIGS. 29-43 show various user interfaces that may be displayed on a workstation, a notebook computer, a terminal, etc. Such user interfaces are optionally written in a mark-up language (e.g., an extensible mark-up language). Such user interfaces may be optionally displayed on a display through use of browser software or other software that interprets mark-up language.

User Interfaces For Managing

To manage information for one or more patients fitted with an implantable device, a service provider may use a computing device that operates management software. Exemplary management software includes a rich set of user interfaces to facilitate information management.

A user interface may include text, graphics, buttons, fields, etc. A user interface may be navigable via an input device such as a mouse, trackball, pen, touchscreen, etc. A user interface may respond to voice commands or signals sent from a handheld or other device. For example, a clinician may scroll down a list of patients presented on the screen of a PDA, select a patient from the list, which, in turn, transmits a signal to a computing device to display information for that patient on a user interface display.

A synchronization feature may exist to synchronize information between a PDA, a cell phone or other device and a workstation setup for managing information. For example, at the end of a day, a clinician may synchronize information stored on a handheld device with information stored in a clinic database.

FIGS. 29-33 pertain to an exemplary user interface system, FIGS. 34-36 pertain to another exemplary user interface system, FIGS. 37-40 pertain to yet another exemplary user interface system and FIGS. 41-45 pertain to another user interface system. While features may be distinct or unique for a particular user interface system, an exemplary user interface system may use any of the variety of features of the systems of FIGS. 29-45 and optionally other features.

Various exemplary user interfaces include interaction structure for viewing transmissions, accessing an archive of past records, and managing patient, clinic, guest accounts, etc. With respect to transmission, transmissions may originate at a housecall device, for example, after the housecall device communicates with an implanted device or another device in a patient's environment.

A user interface system may support layout and functions associated with a list of transmissions (e.g., inbox, preview, physical sorting, transactional inbox, etc.). A user interface system may display information and status records in a list of transmissions.

A user interface may allow for batch printing and exporting records or information from a list of transmission. A user interface system may present information or select a user interface based on a control or an account or log in privilege.

A user interface may allow for notes or annotations, importation of records from external media, and sending records for consultations.

FIG. 29 shows an exemplary user interface 4010. The interface 4010 includes several tabs: Inbox 4012, Archive 4014 and Administration 4016. In this example, the Inbox tab 4012 is selected. The inbox user interface optionally serves as a default task area and displays a list of transmissions received since the last time the clinic account was accessed. The transmission list may be sorted by status (e.g., as a default) or by other criteria. Where status is used, reports with alert appear at the top of the list. This list may continue with transmission for review and transmission that pertain to, for example, a third-party provider.

The user interface 4010 includes several buttons to allow for printing or exporting. For example, a print button can cause printing of a summary list of transmissions while a print selected button can cause printing of various selected records. An export button allows for exporting selected records. The user interface 4010 also allows for printing of individual reports (see, e.g., print button for each patient in the list) and for selecting a patient using a selection box (e.g., a box for each patient in the list located under a SEL column heading). A review button allows a provider to mark reports for review by, for example, a critical decision maker.

Behaviors for action buttons may be configured, for example the 'Print Sel' button may print the full report or just the summary of the selected transmissions.

The exemplary user interface 4010 includes columns for displaying patient name, status of a patient, device identification, time of a transmission or last update, and a summary of patient condition or device condition. In the summary column, conditions such as ventricular tachycardia, ventricular fibrillation, impedance are listed. Such conditions can correspond to one or more trigger parameters. For example, the trigger table 505 includes parameters for ventricular fibrillation, tachycardia and impedance. Thus, an exemplary user interface may display summary information as indicated by a trigger parameter.

An exemplary system includes a trigger table with a condition field. In this example, a trigger causes information to be gated. The gated information includes the condition field, which when received by a server or other device, links the condition field with an exemplary user interface such as the user interface 4010 of FIG. 29. Thus, a user interface may be configured to receive information pertaining to a trigger parameter and to display such information, as appropriate or as desired.

FIG. 30 shows an exemplary user interface 4030 that displays information for a particular patient "Jane Doe", which appeared in the patient name column of the user interface 4010 of FIG. 29. The user interface 4030 includes various buttons such as "view record list" and navigation buttons.

Once a transmission has been selected for review, a user interface system may automatically cause the display of the user interface 4030 where a full summary report is presented, optionally in a scrollable window. The user interface 4030 includes a battery level graphic, an alert information field, information boxes that pertain to device settings for different levels of ventricular tachycardias and for ventricular fibrillation. A field for episodes may summarize information as to types of episodes a patient has experienced.

Figure 31:
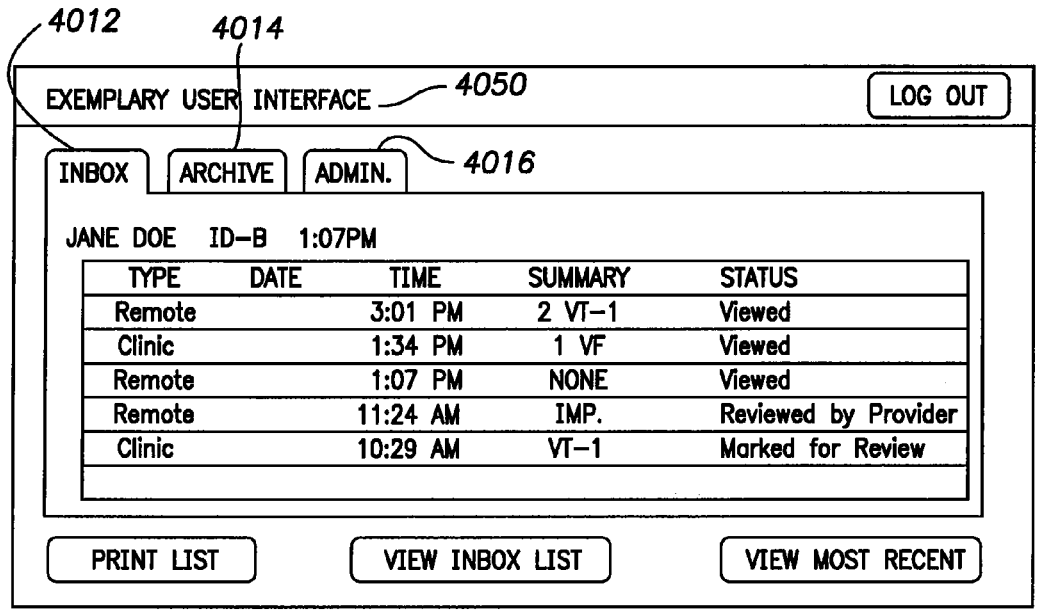

FIG. 31 shows an exemplary user interface 4050 that may appear when a user clicks on the "view all records" button of the user interface 4030 in a patient's individual transmission report. The user interface 4050 includes fields to display an archive of all the remote transmissions and in-clinic reports associated with the selected patient. In the example of FIG. 31, the list is organized chronologically and the user can select an individual report to be viewed. The user interface 4050 includes a button that allows a user to have quick access to the most recent remote transmission for the patient.

An exemplary user interface may provide a button that allows a user to mark a record as "viewed" or "reviewed" or "marked for review". An exemplary user interface may automatically update a record as "viewed" after a user has cause the user interface system to display details for that record. The indicator "reviewed" may be associated with a user account such that only review by a particular user (e.g., primary physician) can cause the indicator to be set to "reviewed".

Figure 32:
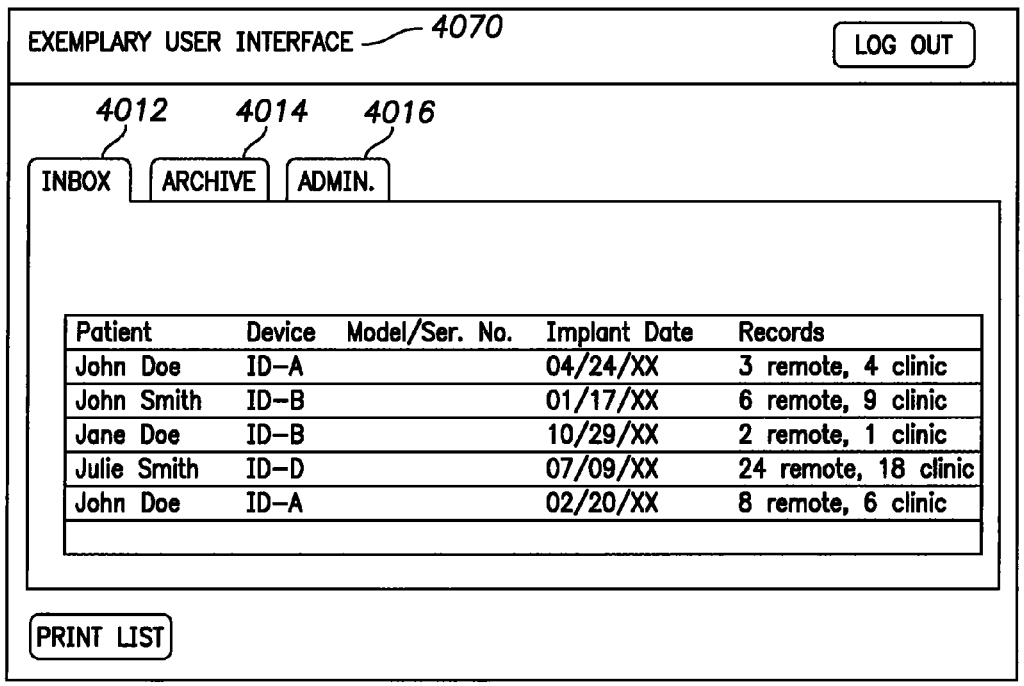

FIG. 32 shows an exemplary user interface 4070 that corresponds to an archive of information for various patients. For example, given any one of the user interfaces of FIGS. 29-31, a user may select the archive tab 4014 to thereby cause a computing device to display the user interface 4070. The user interface 4070 includes fields that list a log of all past remote transmissions and in-clinic reports which have been imported to the archive. For example, the patient "Jane Doe" has listed in a records column, "2 remote, 1 clinic" to represent that the archive includes records for 2 remote transmissions and 1 clinic transmission (e.g., from an in-clinic visit).

An exemplary user interface may be linked to a user's account, for example, based on a user's role. Thus, a critical decision maker such as a clinic's emergency physician may have a user account that causes a user interface system to display a user interface tailored to the emergency physician's role. Such a user interface may display, by default, transmissions with alerts. A list may also exist to indicate transmission designated for additional review by the emergency physician or a person managed by the emergency physician (e.g., an emergency nurse). A button may allow the emergency physician to access other information if needed.

Various lists can be sorted alphabetically by patient, device type, model/serial number, implant date, etc. When a user desires to exit an archive user interface, the user may select a different tab or log out via a log out button.

FIG. 33 shows an exemplary user interface 4090 that corresponds to administrative tasks as the administration tab 4016 is selected. This user interface displays various buttons and information in fields related to administrative tasks.

In the example of FIG. 33, functions include importing in-clinic reports from a programmer via media, enrolling new patients, activating patients who where enrolled at time of implant, and accessing advanced configurations. In this example, access to advanced configurations requires a password. Other fields may be protected as well, especially those for managing user accounts, enrolling clinics and clinicians, and granting special privileges.

A user interface may exist for a patient whereby a patient can access the information via a network such as the Internet. This user interface may include fields for display of basic summary information about the patient's last remote transmission and device. Such a user interface system may provide a patient access to previous transmissions and summaries of in-clinic reports.

Information displayed by a user interface for a patient may include information such as "Your last transmission sent at 09:00 am on 26 Aug. 20XX was received successfully"; "The battery of your St. Jude Medical Epic II+ defibrillator is 78% full"; "Depending on how many episodes you have in the future, your device may last up to 3 more years until the battery needs to be replaced"; "Doing your transmissions when scheduled helps your clinician manage your device better"; "Since your last transmission or in-clinic visit, you have not had any episodes"; and "If you have questions about your heart condition, call your physician"; and "If you have other questions about your device, visit the St. Jude Medical website at www.sjm.com". Where a patient has a housecall device with a user interface display, then such a display may display a patient user interface with the foregoing information or other information.

FIG. 34 shows an exemplary user interface 5010 associated with another exemplary user interface system. The user interface 5010 includes control buttons for an inbox 5012, past reports 5014 and setup 5016. The user interface 5010 corresponds to a home interface that is displayed by a computing device upon log in or upon selection of the inbox button 5012.

The user interface 5010 includes a table with various columns including status, patient name, device identification, time of transmission, alert summary and review. As already mentioned, a summary field may include a condition associated with a trigger parameter. The review field may include information such as reviewed, marked for review, etc., related to review status. The interface 5010 also includes a text and graphics box for display of information for a selected patient.

To access an archive of past records, a user may select the past reports button 5014 and to access advanced configurations, a user may select the setup button 5016.

FIG. 35 shows an exemplary user interface 5030 where a particular patient is selected "Jane Doe". Upon selection of a patient, the user interface 5030 causes information related to that patient to be displayed in the text and graphics box. For example, a battery graphic indicates battery level and other fields provide for display of information such as that presented in the user interface 4030. In the user interface 5030, a user is unable to take any specific actions, like printing or exporting reports.

FIG. 36 shows an exemplary user interface 5050 where a full summary of information for a patient "Jane Doe" is presented. The user interface 5050 includes fields for display of the number of remote transmissions and the number of in-clinic interrogations for the patient "Jane Doe". An annotation box allows for entry of text, which may be saved in association with the patient's records. A check box allows a provider to mark the report for review by an appropriate service provider (e.g., a critical decision maker).

An exemplary user interface may include a "view all" button when a patient's individual transmission report is displayed that causes a computing device to display a list of all the remote transmissions and in-clinic reports. The list may be organized chronologically and a user may sort the list by the column headings. The list may also display any annotations that have been added to a transmission record by a clinician. A "return to current" button can provide quick access back to the most recent remote transmission.

An exemplary user interface system may automatically change a record's status after the record is accessed or may note that the record has been accessed by a particular user. Such access information may be presented as an access history, presentable in a user interface. A table may include a status field that displays a check mark or other graphic when a record has been reviewed by an appropriate service provider.

An exemplary user interface provides fields germane to tasks to be performed by a critical decision maker. For example, upon log in, a system may note the role assigned to the account and select a user interface linked to that role. A critical decision maker may thus see a default user interface that displays urgent transmissions or those marked for additional review. As with other user interfaces, once information has been viewed, an automatic update may occur such as a change in the status column for a patient transmission.

Figures 37, 38:

FIG. 37 shows an exemplary user interface 6010 associated with an exemplary user interface system. The user interface 6010 includes an Inbox tab 6012 and buttons for accessing an archive 6014 and for administration 6016. A table includes columns for status, patient name, device identification, time of transmission and alert summary. Again, the alert summary may be filled with text supplied by a trigger parameter when a gate is opened for transmission of an alert. A "move to completed" button and a "mark for review" button allow a user to manage the transmission presented in the table. Upon selection of a patient and selection of a button, information may be presented in a review text box or a completed text box, as appropriate. The review and completed text boxes include a "remove" button and an "export" button for managing records that appear in the respective text boxes.

FIG. 38 shows an exemplary user interface 6030 that shows a summary of information for a particular patient transmission. This user interface also allows a user to select episodes, diagnosis, tests, parameters associated with the transmission, patient triggers or records.

Additionally, via the user interface 6030, a user can access other user interfaces that provide functions like adding an annotation to be linked with the record, viewing an archive of the patient's past transmissions, and reviewing previous/next records. A print button allows a user to print the specific content which is displayed or the user can print or export the entire report via an "export record" button.

FIG. 39 shows an exemplary user interface 6050 that includes fields for display of information from a record archive for a selected patient. For example, by selecting "View Archive" in the user interface 6030, a user interface system displays the user interface 6050 where fields are filled with information for a selected patient. In the example of FIG. 39, the archive includes three remote transmissions and one clinic transmission. Annotations appear that may summarize action taken or how the condition that caused the transmission was resolved. For example, the remote transmission of 01/06/XX was resolved by resetting parameter Z while the clinic transmission of 03/18/XX was resolved by increasing the level of drug Y. The list of transmissions presented by the user interface 6050 may be organized chronologically or in another manner.

FIG. 40 shows an exemplary user interface 6070 where a transmission record for patient "Jane Doe" has been annotated in an annotation field. This user interface also includes an approved field and buttons to move transmission records to the approved field and thereby mark the records as approved.

FIG. 41 shows an exemplary user interface 7010 associated with an exemplary user interface system. The user interface 7010 includes buttons for transmissions, patients and clinicians. The interface 7010 appears as a default upon log in or upon selection of the transmissions button. The user interface 7010 shows an inbox with a table of transmissions with column headings selection (SEL), patient name, device, time of transmission (including date where appropriate) and summary. Again, the summary field of the table may display information from a trigger parameter for a trigger that cause information to be gated and hence the transmission to occur.

The table also includes a drop down menu with various actions, such as, review, completed, print and export. A user may select an action from the drop down menu for a particular patient transmission.

The user interface 7010 includes a Inbox transmission counter (e.g., 22 transmissions) and counters for reviewed transmissions and completed transmissions. Various buttons allow actions such as "Print Selection", "Export Selection" and "Print List". A selection box "select all items" allows a user to select all items in the Inbox. A clinician may select all items and then print the list and review off-line. Once the clinician has finished reviewing one or more of the transmissions, the clinician may log in and select a completed or other appropriate action from the drop down menu. Once a user selects "completed" the user interface may cause a computing device to move the record to an archive or to change an indicator associated with the transmission record to indicate that it is now an archive item.

The user interface 7010 may cause a full report user interface to be displayed when a user clicks on the name of a patient. Thus, the name field of the table may be active and link to another user interface. The summary field may be linked to a description table that provides for a description of the summary information. Alternatively, a bubble may appear once a cursor is placed on the summary field in the table where the bubble displays information about the summary for the transmission.

FIG. 42 shows an exemplary user interface 7030 that corresponds to selection of the "patients" button. This user interface displays various buttons and fields related to patient records. For example, a search field may include a drop down list of clinics, an "enter patient name" button may present a text field for entry of a patient's name or part of a patient's name. A browse button allows a user to browse data stores for importation of records. Such a browse button may optionally allow for browsing to a patient's housecall device. For example, a housecall device may appear as a drive or a folder in a network directory. In this manner, a user may pull information resident on a patient's housecall device, whether the information has already been sent or is to be sent.

An enroll button allows a user to enroll a patient into a management system. An activate button allows a user to activate a patient with a new implant and housecall device. Drop down menus list clinics and once a clinic is selected, another drop down menu lists new patients associated with the selected clinic. Once the patient is identified, a user may select the activate button to thereby activate an account for that patient (e.g. a directory, an identification, etc.). Upon activation, a signal may be transmitted to a patient's housecall device that notifies the patient of the activation.

The user interface 7030 includes a "clinicians" button that, once selected, causes a user interface system to display an exemplary user interface for clinician tasks. FIG. 43 shows an exemplary user interface 7050 that includes various buttons such as "select patient", "triggers", "medications", and "therapy". Also shown are various columns such as those of table 505 of FIG. 6. The column "QL" for "query logic" may be set as shown in FIG. 45.

In the example of FIG. 43, the triggers button is highlighted and a trigger table is presented for a selected patient "Jane Doe". A user may, given appropriate permission, alter one or more trigger parameters in the table, add a trigger or delete a trigger.

A "logic" button allows a user to view logic and timing of triggers based on the trigger table, past history or a simulation. FIG. 44 shows an exemplary user interface with a logic graphic that lists various triggers, timing and trigger-to-trigger interaction. Such logic may allow a user to more appropriately set triggers to avoid avalanches or cascades of information that could result in multiple redundant transmissions.

Figure 45:
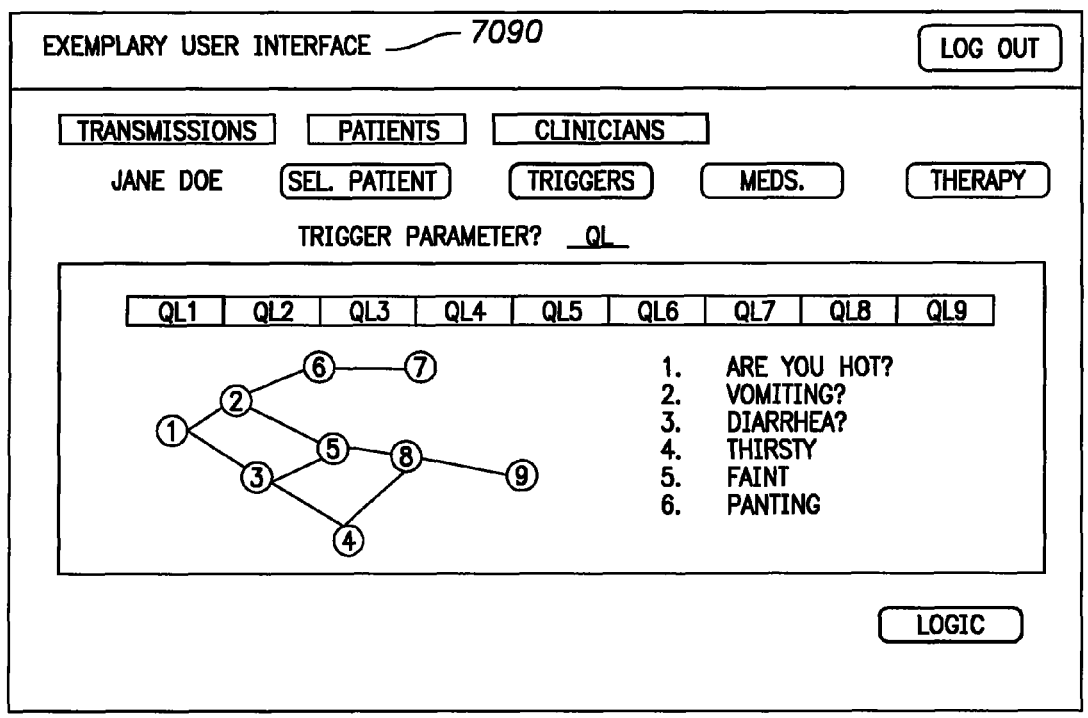

FIG. 45 shows an exemplary user interface 7090 with a query logic graphic. A user may optionally select a specific trigger parameter and then view or revise the parameter. For example, the query logic parameter QL1 shows a decision tree where each node of the tree corresponds to a particular question. Not shown in this tree is the underlying logic that uses one or more answers to analyze information or to make decisions, other than progressing to a particular query. In general, the branches of the tree correspond to yes/no bifurcations or other paths that may depend on an answer to a query. The query logic may be tailored to particular device capabilities. For example, where a device includes a LED display, a patient may have a code chart to understand the questions presented. Where a device includes a speaker, then the questions may be presented audibly and where a device includes a text display, the questions may be presented visually, etc. With respect to a audibly message, the user interface 7090 includes a button for recording a voice. For example, a clinician may select the record button and then record a question for use in the query logic. The recorded voice message may be stored as a digital file (compressed or uncompressed) and transmitted to a location for use or transmitted on an as needed basis. Alternatively, a clinician may selected a pre-recorded audio message or, as already mentioned, a text or other type of message or indicator to present a query to a patient or a person caring for a patient.

The use of query logic can increase accuracy of diagnostic information as well as provide a direct indication of a patient's coherency or condition. With respect to coherency, a time interval may be measured from the time a query is presented to a user until the time an answer is entered (e.g., by pushing a button, speaking into a microphone, etc.). Such response time information may be used to assess quality of answers, which may depend on patient condition.

As described herein various exemplary user interfaces can facilitate administration of patient information and therapy management. An exemplary computer system having a graphical user interface including a display and a user input device may be used to implement a method for administrating patient records where the method includes displaying an inbox tab or button and one or more other tabs or buttons, receiving an entry selection signal indicative of the user input device selecting the inbox tab or button and, in response to the selection signal, displaying patient records wherein the displaying comprises displaying a patient status field for each patient record, displaying a device field for each patient record, and displaying a review button for each patient record.

Such an exemplary method may further include receiving an entry selection signal indicative of the user input device selecting the review button for a patient record and, in response to the selection signal, displaying a battery level field for an implantable device associated with the patient record. As shown in various figures, in response to a selection signal, a method may include displaying one or more episodes fields for arrhythmic episodes experienced by the patient corresponding to the patient record as indicated by data received from an implantable device associated with the patient, the device identified in the device field.

An exemplary method may include displaying text in a text field that indicates a number of transmissions received by an inbox of a user since a given time and that indicates a number of transmissions viewed by the user.

An exemplary method may rely on a computer system having a graphical user interface including a display and a user input device to perform the steps of displaying an archive tab or button and one or more other tabs or buttons, receiving an entry selection signal indicative of the user input device selecting the archive tab or button and, in response to the selection signal, displaying patient records wherein the displaying comprises displaying a patient name field for each patient record, displaying a device field for each patient record, and displaying a records field for each patient record wherein the records field comprises a numeric field for a number of archived records associated with remote communication and a numeric field for a number of archived records associated with in-clinic communication.

An exemplary method may rely on a computer system having a graphical user interface including a display and a user input device to perform the steps of displaying an administration tab or button and one or more other tabs or buttons, receiving an entry selection signal indicative of the user input device selecting the administration tab or button and, in response to the selection signal, displaying an import button for importing patient records, displaying an enroll button to enroll a patient for a remote transmission program, displaying a clinic menu for listing participating clinics, displaying a patient menu for listing eligible patients associated with a participating clinic. Such a method may include receiving an entry selection signal indicative of the user input device selecting a clinic from the clinic menu and, in response to the selection signal, displaying in the patient menu a list of eligible patients associated with the selected clinic.

An exemplary method may rely on a computer system having a graphical user interface including a display and a user input device to perform the steps of displaying a transmissions button and one or more other buttons, receiving an entry selection signal indicative of the user input device selecting the transmissions button and, in response to the selection signal, displaying patient records wherein the displaying comprises displaying a patient name field for each patient record, displaying a device field for each patient record, and displaying a menu for each patient record wherein the menu comprises at least one menu entry selected from a group consisting of review, completed, print and export.

An exemplary method may include displaying a clinicians button and one or more other buttons, receiving an entry selection signal indicative of the user input device selecting the clinicians button and, in response to the selection signal, displaying a select patient button, a triggers button, a medications button and a therapy button. Such a method may include receiving an entry selection signal indicative of the user input device selecting the triggers button and, in response to the selection signal, displaying a trigger table. Selection of a query logic trigger parameter may cause display of a decision tree for query logic. Further, such a method may display text fields that present queries for use in constructing query logic.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
setting a trigger configured to control information flow;
transmitting the trigger to a computing device in a patient environment;
acquiring information in the patient environment using the computing device wherein the information comprises data from an implantable device;
analyzing the information with respect to the trigger in the patient environment;
presenting a query to a patient in the patient environment using the computing device;
receiving an answer to the query from the patient; and
deciding whether to transmit information via a network to a clinical environment based on the analyzing and based on the answer, wherein if the answer comprises a first response then the deciding comprises transmitting the information to the clinical environment, and if the answer comprises a second answer then the deciding comprises declining to transmit the information to the clinical environment.

2. The method of claim 1 wherein the trigger comprises trigger parameters.

3. The method of claim 1 wherein the trigger parameters comprise at least one parameter selected from a group consisting of a condition parameter, a numeric criterion parameter, an alert level parameter, a destination parameter, a permission parameter, a message parameter and a query logic parameter.

4. The method of claim 1 wherein the trigger comprises a numeric value representative of impedance.

5. The method of claim 1 wherein the trigger comprises a numeric value representative of heart rate.

6. The method of claim 1 wherein the trigger comprises a numeric value representative of time.

7. The method of claim 1 further comprising deciding whether to perform the setting after deciding to transmit information.

8. The method of claim 1 wherein if the deciding decides to transmit information via a network to a clinical environment, an alert level accompanies the transmission.

9. The method of claim 1 wherein if the deciding decides to transmit information via a network to a clinical environment, the trigger provides an address for the clinical environment.

10. The method of claim 1 wherein if the deciding decides to transmit information via a network to a clinical environment, a condition indicator accompanies the transmission.

11. A method comprising:
acquiring information in a patient environment using a computing device wherein the information comprises data from an implantable device;
presenting a query to a patient in the patient environment using the computing device;
receiving an answer to the query from the patient via the computing device; and
deciding whether to transmit information via a network to a clinical environment based at least in part on the answer, wherein the deciding comprises declining to transmit the information if the answer comprises a first response to the query.

12. The method of claim 11 further comprising deciding whether to present another query based on the answer.

13. The method of claim 11 further comprising analyzing the acquired information and presenting the query based at least in part on the analyzing.

14. The method of claim 11 further comprising providing a trigger.

15. The method of claim 11 further comprising analyzing the information with respect to the trigger and presenting the query based on the analyzing.

16. A system comprising:
- means for acquiring data from an implantable device;
- means for presenting a query to a patient in the patient environment in response to the data;
- means for receiving an answer to the query from the patient; and
- means for declining to transmit the information to a clinical environment based at least in part on the answer.

* * * * *